(12) United States Patent
Takagi et al.

(10) Patent No.: US 7,001,019 B2
(45) Date of Patent: Feb. 21, 2006

(54) IMAGE OBSERVATION APPARATUS AND SYSTEM

(75) Inventors: Akinari Takagi, Yokosuka (JP); Tsutomu Osaka, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 365 days.

(21) Appl. No.: 09/838,219

(22) Filed: Apr. 20, 2001

(65) Prior Publication Data

US 2002/0051118 A1 May 2, 2002

(30) Foreign Application Priority Data

Oct. 26, 2000 (JP) .......................................... 2000-326753
Nov. 16, 2000 (JP) .......................................... 2000-349238

(51) Int. Cl.
*A61B 3/10* (2006.01)

(52) U.S. Cl. ...................................................... 351/211
(58) Field of Classification Search ................. 351/200, 351/205, 209, 211, 213, 216, 221; 348/42, 348/51, 52, 55, 56, 57, 58, 59, 60
See application file for complete search history.

(56) References Cited

U.S. PATENT DOCUMENTS

| | | | | |
|---|---|---|---|---|
| 5,231,674 A | * | 7/1993 | Cleveland et al. | .......... 351/210 |
| 5,610,673 A | * | 3/1997 | Rafal et al. | .................. 351/209 |
| 5,703,637 A | * | 12/1997 | Miyazaki et al. | .............. 348/53 |
| 5,714,967 A | | 2/1998 | Okamura et al. | |
| 5,719,701 A | | 2/1998 | Sudo | |
| 5,825,539 A | | 10/1998 | Hoshi | |
| 6,023,373 A | * | 2/2000 | Inoguchi et al. | ............ 359/631 |
| 6,094,241 A | * | 7/2000 | Yamazaki | ..................... 349/11 |
| 6,229,561 B1 | | 5/2001 | Son et al. | |
| 6,233,003 B1 | | 5/2001 | Ono | |
| 6,377,295 B1 | * | 4/2002 | Woodgate et al. | ........... 359/463 |
| 6,417,895 B1 | * | 7/2002 | Tabata et al. | .................. 349/11 |
| 2002/0034016 A1 | * | 3/2002 | Inoguchi et al. | ............ 359/630 |
| 2002/0036750 A1 | * | 3/2002 | Eberl et al. | .................. 351/207 |

FOREIGN PATENT DOCUMENTS

| | | |
|---|---|---|
| DE | 10047237 A1 * | 4/2002 |
| JP | 07-311361 | 11/1995 |
| JP | 08-211325 | 8/1996 |
| JP | 08-334730 | 12/1996 |
| JP | 09-166760 | 6/1997 |
| JP | 09-281438 | 10/1997 |
| JP | 10-111475 | 4/1998 |
| JP | 2001-42257 | 2/2001 |

OTHER PUBLICATIONS

Yoshihiro Kajiki, "3–D Display in which Super Multi–Eye Area is Employed," Optical and Electro–Optical Contact, vol. 26, No. 11, Nov. 20, 1998, Japan Optoelectro–Mechanics Association, pp. 624–631. (with English translation).

* cited by examiner

*Primary Examiner*—Brian L. Casler
*Assistant Examiner*—John R Sanders
(74) *Attorney, Agent, or Firm*—Fitzpatrick, Cella, Harper & Scinto

(57) ABSTRACT

An image observation apparatus is constructed to project image information displayed on an image display device for displaying the image information, onto a retina of an observing eye by a display optical system, thereby permitting an observer to observe the image information, and to perform control to change a position of an incident beam onto the entrance pupil plane of the observing eye. The apparatus is arranged to detect the position of the observer's pupil and change the position of the incident beam onto the entrance pupil plane of the observing eye, based on the result of the detection.

23 Claims, 24 Drawing Sheets

IMAGE OBSERVATION APPARATUS AND SYSTEM

BACKGROUND OF THE INVENTION

1. Field of the Invention

The present invention relates to image observation apparatus for projecting image information directly onto the retina of an observing eye to permit observation thereof and an image observation system using the apparatus, and to image observation apparatus for causing a plurality of parallax images to be incident on a single eye to permit an observer to observe a three-dimensional image in a natural state without causing fatigue of the observer's eye and an image observation system using the apparatus, which are particularly suitable for three-dimensional display and three-dimensional observation in a wide angle of view.

2. Related Background Art

The image observation apparatus of the type for directly projecting an image onto the retina has been known heretofore as apparatus for permitting observation of image information based on image display means such as a liquid crystal display panel or the like. For example, the method disclosed in Japanese Patent Publication No. 2679176 permits the observation of image information in similar fashion to the principle of pinhole camera, by illuminating a display element by a point light source and focusing an image of the point light source on the entrance pupil of the observer. This construction allows the observer to observe clear image information, independent of the imaging performance of eye.

For observation of a stereoscopic image, a pair of image observation devices are provided for the left and right eyes to effect stereoscopic vision by use of binocular parallax. In this construction, focusing conditions of observed images are independent of the accommodation of the eyes. Therefore, this construction can reduce contradiction between convergence and accommodation of the observing eyes in observation of the stereoscopic image by use of only the binocular parallax, so that the observer can observe the stereoscopic image well in the natural state.

The image observation apparatus of the type for directly projecting the image onto the retina is not suitable for observation of image information in a wide angle of view, because the size of an incident beam is fundamentally small at the position of the entrance pupil of the observing eye. This is because, as illustrated in FIGS. 38A and 38B, when the eyeball E is rotated around the rotational center C of eyeball so as to gaze at the marginal part of the field, a difference is made in the relation between the rotational center C of eyeball and the position of the pupil P (entrance pupil) and the beam is intercepted by the iris I because of change of the position of the pupil P to fail to enter the eyeball, thus disabling observation.

FIG. 38A shows a situation in which the eye is gazing at the center of the field of image information, wherein display rays 200 travel through the pupil P without being intercepted by the iris I, to enter the observing eye E. However, when the eyeball E is rotated in order to gaze at the marginal part of the field as illustrated in FIG. 38B, the display rays 200 are intercepted by the iris I to fail to enter the observing eye E. Symbol L indicates the direction of the visual axis.

An object of the present invention is to provide image observation apparatus capable of guiding rays into the eyeball without interception at the iris even in the eyeball state rotated from the center of the field to gaze at the marginal part of the field during observation of the image information displayed on image display means, thus implementing display and observation in a wide angle of view, and capable of reproducing a space in a wide range in the depth direction during observation of a stereoscopic image, and also provide an image observation system using the apparatus.

On the other hand, various proposals have been made heretofore on methods of reproducing the stereoscopic image. Popular methods among these are methods of realizing observer's stereoscopic vision by use of binocular parallax (polarizing spectacles methods, lenticular methods, and so on). In addition, in order to avoid the contradiction between accommodation and convergence of eyes, some attempts have been made to develop methods of reproduction of three-dimensional image satisfying the other stereoscopic recognition function of eye, without relying on only the binocular parallax.

According to Chapter 3, Paragraph 8 "Studies about stereoscopic vision of super-multiview regions" in the publication "Final outcome reports of advanced stereoscopic motion picture communication project" issued in 1997 by Telecommunications Advancement Organization of Japan, it is reported that, under stereoscopic display of "super-multiview regions" in which the view point is sampled at a frequency higher than the spatial frequency of the pupil and in which continuous parallax is reproduced as in the case of an actually existing object, a plurality of parallax images are incident to a single eye of an observer and this presents the effect of guiding the accommodation of focus of the observer's eye to near a pseudo stereoscopic image induced by the binocular parallax, thereby reducing fatigue and dysphoria of the observer. Namely, the publication describes the remark that stereoscopic display with less fatigue of eye is achieved by the "monocular parallax effect" when the conventional stereoscopic display method of presenting parallax images from two view points to the two eyes is extended to a method of presenting parallax images from n view points to n view points and when the distance between two adjacent points of the n view points is set smaller than the observer's pupil.

However, for implementing the stereoscopic display of the "super-multiview regions," it is necessary to present extremely small parallax images to the observer and it thus becomes necessary to handle very huge volumes of image information. In addition, an extremely quick information display means is necessary, because all the parallax images need to be displayed within the permissible time for persistence of vision of the observer's eye.

In Japanese Patent Application No. 2000-28853 filed by Assignee of the present application, we proposed the image observation apparatus capable of implementing the stereoscopic display of "super-multiview regions" without use of very quick image display means and image generating means nor many image display means. This method is characterized in that an exit pupil of a display optical system is optically divided into a plurality of regions, parallax images corresponding to the respective regions are guided to each observer's eye to cause the parallax images to be incident on the single eye, and image observation devices are provided respectively for the left and right eyes, thereby reducing the number of parallax images to be displayed on each image observation device.

For constructing the image observation apparatus capable of displaying the stereoscopic image in a wide angle of view, it is necessary to set the size of the exit pupil of the display optical system to a large value in order to adapt for movement of the position of the pupil (entrance pupil) with motion of the visual axis for the observer to gaze at the marginal part of the observation field. For example, when the display view angle in the horizontal direction is $2\theta$ as illustrated in FIG. 37, the minimum horizontal width necessary for the exit pupil of the display optical system is given by $2 \times L \times \sin\theta$. Here L indicates the distance between the eyeball rotation center $O1$ and the entrance pupil P of the observing eye and is about 10 mm. For example, when $2\theta=30°$, the horizontal width of the exit pupil is 5.2 mm. When $2\theta=50°$, the horizontal width is 8.5 mm. In practice, values of about 8 mm and 12 mm are adopted in the cases of $2\theta=30°$ and $2\theta=50°$, respectively, including some margins for the above-stated values in consideration of sizes of pupils, deviation upon mounting, and so on.

For making a plurality of parallax images incident on a single eye, spacings between centers of the respective regions obtained by dividing the area of the exit pupil into plural regions need to be smaller than the size of the observer's pupil; specifically, about 2 mm, for example, Namely, the size of each region has to be not more than a predetermined size, irrespective of the display view angle.

For the above reasons, many parallax images have to be generated and displayed in order to provide the image observation apparatus permitting the observation of the stereoscopic image in a wide angle of view, and it thus becomes necessary to use very quick image display means and image generating means and many image display means.

Another object of the present invention is thus to provide image observation apparatus being capable of implementing the stereoscopic display of the super-multiview regions in a wide angle of view and thus permitting the observer to observe the stereoscopic image well without fatigue nor dysphoria, and to provide an image observation system using the apparatus.

SUMMARY OF THE INVENTION

An image observation apparatus according to an aspect of the present invention is an image observation apparatus for observing image information, comprising:

image display means for displaying image information;

a display optical system for projecting the image information displayed on the image display means, onto a retina of an observing eye; and incident beam control means for changing a position of an incident beam on an entrance pupil of the observing eye.

In a further aspect of the above image observation apparatus, the position of the incident beam on the plane of the entrance pupil of the observing eye is changed by the incident beam control means in accordance with the image information displayed on the image display means.

In a further aspect of the above image observation apparatus, the apparatus further comprises pupil position detecting means for detecting a position of a pupil of the observer, and the position of the incident beam on the plane of the entrance pupil of the observing eye is changed by the incident beam control means, based on information obtained by the pupil position detecting means.

In a further aspect of the above image observation apparatus, the pupil position detecting means comprises eyeball illuminating means and light receiving means for receiving light reflected by the eyeball from illumination light emitted from the eyeball illuminating means, and the eyeball illumination light is infrared light.

In a further aspect of the above image observation apparatus, the apparatus comprises illumination means for illuminating the image display means, an illumination light source of the illumination means is imaged at or near the position of the entrance pupil of the observing eye by the display optical system, and the position of the incident beam on the plane of the entrance pupil of the observing eye is changed by controlling an emission state of the illumination means.

In a further aspect of the above image observation apparatus, the image display means comprises a transmission type spatial modulation element.

In a further aspect of the above image observation apparatus, the image display means comprises a reflection type spatial modulation element.

In a further aspect of the above image observation apparatus, the illumination means comprises a light-emitting element array.

In a further aspect of the above image observation apparatus, the illumination means comprises a surface illuminant and a spatial modulation element.

In a further aspect of the above image observation apparatus, the illumination means comprises a substantially point light source and an optical system having a positive power.

In a further aspect of the above image observation apparatus, the image display means is a self-emission type or light-source-integrated type display element, the image observation apparatus comprises a spatial modulation element for limiting light from the image display means, the spatial modulation element is imaged at or near the position of the entrance pupil of the observing eye by the display optical system, and the position of the incident beam on the plane of the entrance pupil of the observing eye is changed by controlling the spatial modulation element.

In a further aspect of the above image observation apparatus, the spatial modulation element is a transmission type spatial modulation element having a two-dimensional pixel structure.

In a further aspect of the above image observation apparatus, the spatial modulation element is a reflection type spatial modulation element having a two-dimensional pixel structure.

An image observation apparatus according to another aspect of the present invention is an image observation apparatus comprising image display means for displaying a plurality of parallax images, and a display optical system for guiding light from the image display means to an observing eye of an observer, the image observation apparatus being constructed to spatially divide an exit pupil of the display optical system into a plurality of regions, substantially align a position of the exit pupil of the display optical system with a position of an entrance pupil of the observing eye, cause parallax images corresponding to the respective regions to be incident on the observing eye, and thereby cause a plurality of parallax images to be incident on the single eye of the observer, wherein an area of a region in the outermost periphery out of the plurality of regions in the divided exit pupil is greater than those of the regions except for that in the outermost periphery.

An image observation apparatus according to still another aspect of the present invention is an image observation apparatus comprising image display means for displaying a plurality of parallax images, and a display optical system for guiding light from the image display means to an observing eye of an observer, the image observation apparatus being constructed to spatially divide an exit pupil of the display optical system into a plurality of regions, substantially align a position of the exit pupil of the display optical system with a position of an entrance pupil of the observing eye, cause parallax images corresponding to the respective regions to be incident on the observing eye, and thereby cause a plurality of parallax images to be incident on the single eye of the observer, wherein a size of the exit pupil of the display optical system is larger than a size of the entrance pupil of the observing eye and a size of a beam from the image display means at the position of the entrance pupil of the observing eye is substantially equal to or smaller than the size of the entrance pupil of the observing eye, and the image observation apparatus comprises control means to change a position of the beam from the image display means at the position of the entrance pupil of the observing eye.

In a further aspect of the above image observation apparatus, the apparatus further comprises pupil position detecting means for detecting the position of the pupil of the observer, and the position of the beam from the image display means at the position of the entrance pupil of the observing eye is changed by the control means, based on information obtained by the pupil position detecting means.

In a further aspect of the above image observation apparatus, the pupil position detecting means comprises eyeball illuminating means and light receiving means for receiving light reflected by the eyeball from illumination light emitted from the eyeball illuminating means, and the eyeball illumination light is infrared light.

In a further aspect of the above image observation apparatus, the apparatus comprises illumination means having an illumination light source for illuminating the image display means, the illumination means is located at or near a position optically equivalent to the entrance pupil of the display optical system, the illumination means comprises a plurality of unit light sources, images of the plurality of unit light sources are formed in a plurality of regions in the exit pupil of the display optical system, the exit pupil of the display optical system is spatially divided into a plurality of irradiation regions, and a display image on the image display means is controlled to switch to one corresponding to each irradiation region.

In a further aspect of the above image observation apparatus, the plurality of unit light sources of the illumination light source are comprised of a light-emitting element array.

In a further aspect of the above image observation apparatus, the plurality of unit light sources of the illumination light source are comprised of a surface illuminant and a spatial modulation element.

In a further aspect of the above image observation apparatus, the image display means comprises a plurality of display elements, the image observation apparatus comprises at least one illumination means having an illumination light source for illuminating the plurality of display elements, the illumination means is located at or near a position optically equivalent to the entrance pupil of the display optical system, the illumination means comprises a plurality of unit light sources, images of the plurality of unit light sources are formed in a plurality of regions in the exit pupil of the display optical system, the exit pupil of the display optical system is spatially divided into a plurality of irradiation regions, and parallax images displayed on the plurality of display elements are controlled corresponding to each irradiation region.

In a further aspect of the above image observation apparatus, the illumination means is a plurality of illumination means, incidence of beams into a plurality of regions in the exit pupil of the display optical system is controlled in time division by controlling in time division irradiation of beams from a plurality of unit light sources which an illumination light source of each illumination means has, and parallax images displayed on the plurality of display elements are controlled to switch to those corresponding to each region.

In a further aspect of the above image observation apparatus, the plurality of unit light sources of the illumination light source are comprised of a light-emitting element array.

In a further aspect of the above image observation apparatus, the plurality of unit light sources of the illumination light source are comprised of a surface illuminant and a spatial modulation element.

In a further aspect of the above image observation apparatus, the image display means comprises a self-emission type image display element or a light-source-integrated type image display element, the display optical system comprises a relay optical system for forming an aerial image of a surface of the image display element and an eyepiece optical system for presenting an enlarged virtual image of the aerial image to the observing eye, a spatial modulation element having a two-dimensional pixel structure is located at or near a position of an entrance pupil of the eyepiece optical system, images of the spatial modulation element divide the exit pupil of the display optical system into a plurality of regions, beams incident to the plurality of regions in the exit pupil of the display optical system are controlled by controlling irradiation of beams from respective pixels of the spatial modulation element, and parallax images displayed on the image display means are controlled to switch to those corresponding to circumstances of incidence of a beam into the each region.

In a further aspect of the above image observation apparatus, the spatial modulation element is a transmission type spatial modulation element.

In a further aspect of the above image observation apparatus, the spatial modulation element is a reflection type spatial modulation element.

In a further aspect of the above image observation apparatus, the display optical system comprises a prism body having a decentered, rotationally asymmetric, reflective surface with optical powers differing depending upon azimuth angles.

An image observation system according to one aspect of the present invention is an image observation system comprising a pair of image observation apparatus as set forth, for the left and right eyes of the observer.

DETAILED DESCRIPTION OF THE PREFERRED EMBODIMENTS

Figure 1:
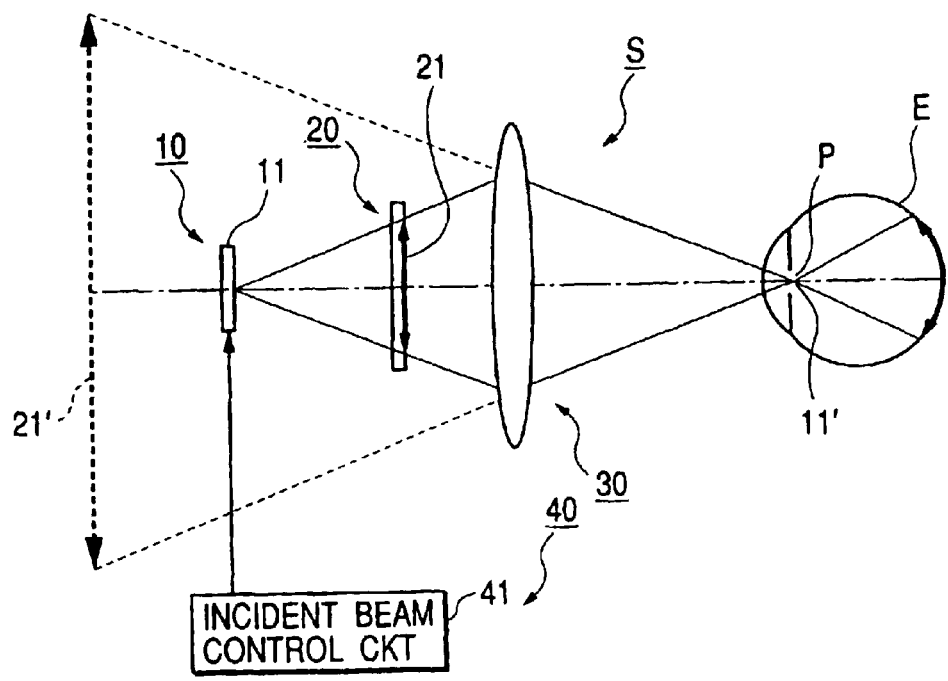
FIG. 1 is an explanatory diagram to illustrate the basic concept of the optical system of image observation apparatus according to an aspect of the present invention.
Figure 2:
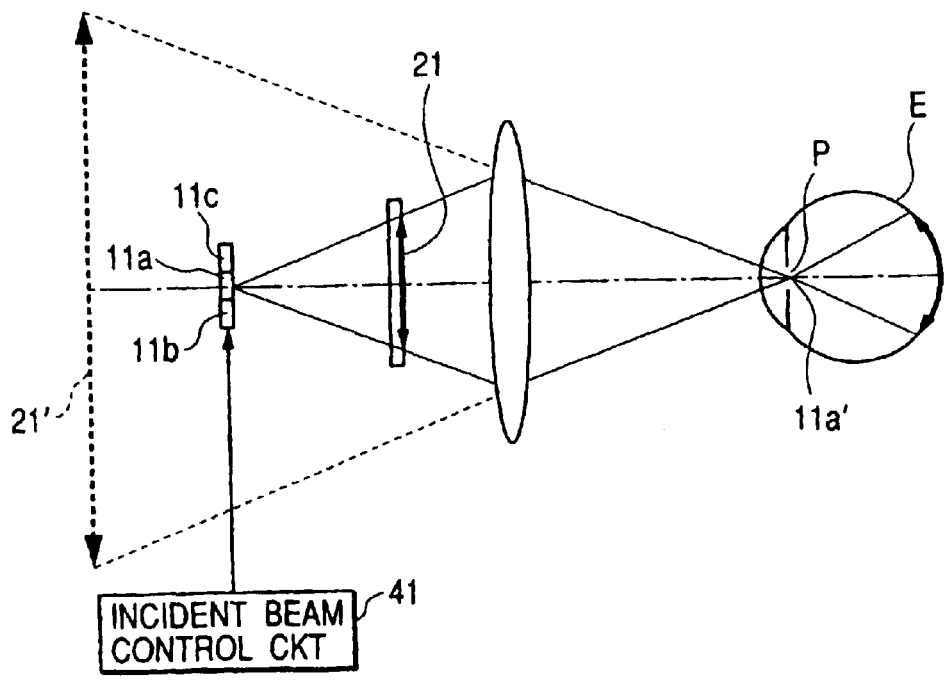
FIG. 2 is an explanatory diagram to illustrate the basic concept of the optical system of image observation apparatus according to the aspect of the present invention.
Figure 3:
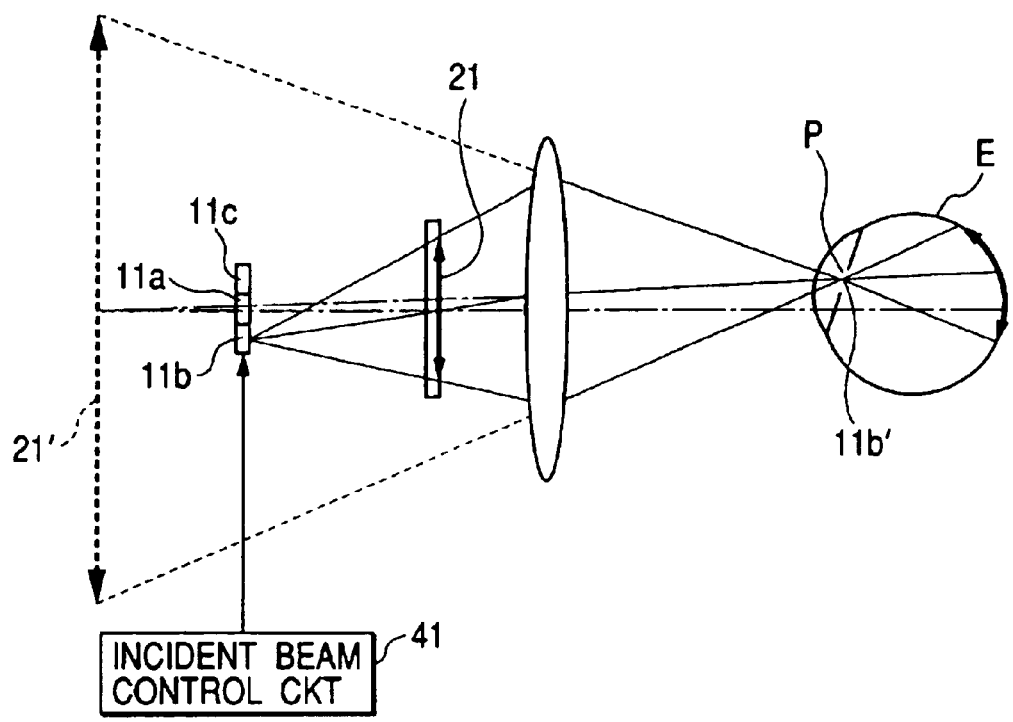
FIG. 3 is an explanatory diagram to illustrate the basic concept of the optical system of image observation apparatus according to the aspect of the present invention.

FIG. 1 to FIG. 3 are explanatory diagrams to illustrate the basic concept of the image observation apparatus of the present invention.

The image observation apparatus S according to the present invention is generally provided with an illumination means 10 having an illumination light source 11, an image display means 20 for displaying image information 21, a display optical system 30, and a control means 40.

In FIG. 1, the display optical system 30 forms an image 11' of the illumination light source 11 at or near the position of the pupil (entrance pupil) P of the observing eye E. At this time the size of the illumination light source 11, the position and focal length of the display optical system 30, etc. are set so that the size of the illumination light source image 11' becomes sufficiently smaller than the size of the pupil P of the observing eye E. The display optical system 30 directly projects the image information 21 onto the retina of the observing eye E or guides beams from the image information 21 through the entrance pupil P onto the retina of the observing eye E. The observer observes an image (enlarged virtual image) 21' formed by the display optical system 30 from the image information 21 displayed on the image display means 20 under illumination by the illumination means 10.

An incident beam control circuit 41 controls the illumination means 10, based on the image information and output from pupil position detecting means described hereinafter, to change the position of a light-emitting surface or light-emitting point of the illumination light source 11, thereby changing the position of the incident beam at the position of the pupil P of the observing eye E.

The illumination light source 11 consists of a plurality of unit light sources (11a, 11b, . . . ) and, as illustrated in FIG. 2 and FIG. 3, the incident beam control circuit 41 lights up at least one of the unit light sources 11a to 11c according to the position of the observer's pupil P. FIG. 2 shows a situation in which the observer is gazing at the center of the field of the image information 21, and the incident beam control circuit 41 controls the illumination means 10 to light up the unit source 11a. The display optical system 30 forms a light source image 11'a on the pupil P of the observing eye E, so that the observer can observe the image 21' formed by the display optical system 30 from the image information 21. When the observer is gazing at the marginal part of the field of the image information 21, as illustrated in FIG. 3, the incident beam control circuit 41 controls the illumination means 10 to light up the unit light source 11b. The display optical system 30 forms a light source image 11'b on the pupil P of the observing eye E, so that the observer can observe the image 21' formed by the display optical system 30 from the image information 21.

Since the size of the incident beam is small at the position of the entrance pupil P of the observer in this construction, the observer can observe a clear image of the image information 21, independent of the imaging performance of the eye optical system of the observer, on the basis of the principle similar to the so-called pinhole camera. Since the beam is incident to the eye without being intercepted even during the gaze at the marginal part of the field of the image information 21, it becomes feasible to implement the display and observation in the wide angle of view.

FIG. 4 to FIGS. 9A to 9C show several configurations of specific operations of the illumination light source 11 of the illumination means 10.

Figure 4:
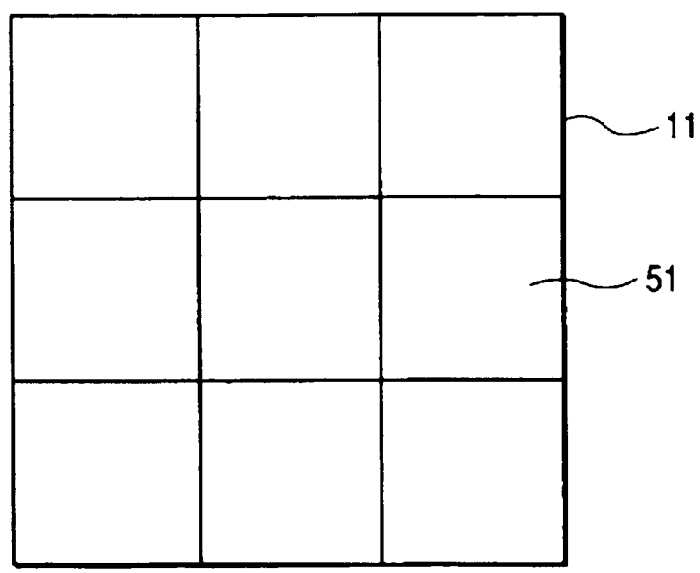
FIG. 4 is an explanatory diagram to illustrate the illumination means in the image observation apparatus of the present invention.

For example, as illustrated in FIG. 4, the illumination light source 11 is comprised of a plurality of unit light sources 51 resulting from area-based division of the total area of the light source 11 into a plurality of regions. The incident beam control circuit 41 lights up each unit light source according to the position of the pupil of the observing eye.

The illumination light source 11 is constructed as a light-emitting element array such as an EL panel or an LED array, or in either of the configurations as illustrated in FIGS. 5 to 8.

Figure 5:
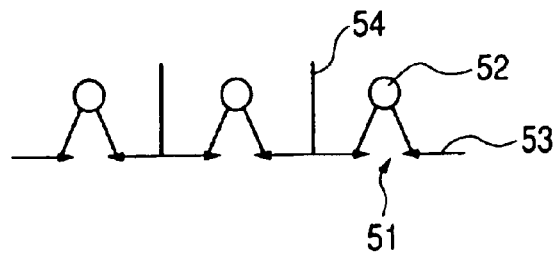
FIG. 5 is an explanatory diagram to illustrate the illumination means in the image observation apparatus of the present invention.

In FIG. 5, a unit light source 51 consists of a light-emitting element 52 and a pinhole 53 illuminated with a beam therefrom. Shield plates 54 are provided for preventing beams from adjacent light-emitting elements 52 from leaking into the light-emitting element 52 of interest.

Figure 6:
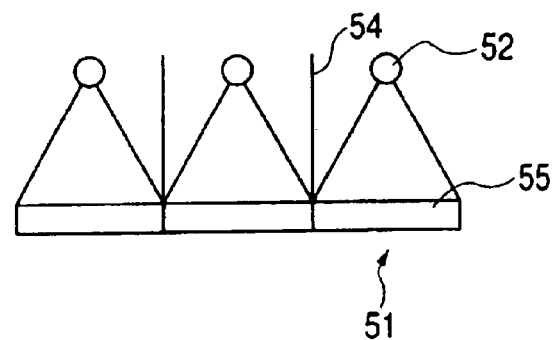
FIG. 6 is an explanatory diagram to illustrate the illumination means in the image observation apparatus of the present invention.

In FIG. 6, a unit light source 51 consists of a light-emitting element 52 and a diffuser plate 55 illuminated by a beam therefrom. Shield plates 54 are provided for preventing beams from adjacent light-emitting elements from leaking into the light-emitting element of interest.

Figure 7:
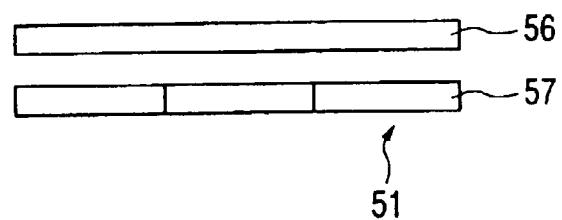
FIG. 7 is an explanatory diagram to illustrate the illumination means in the image observation apparatus of the present invention.

In FIG. 7, the illumination light source 11 consists of a surface emitting light source (surface illuminant) 56 such as a cold-cathode tube and a lightguide plate, or the like, and a transmission type spatial modulation element 57 such as a transmissive liquid crystal panel or the like. A unit light source 51 is comprised of one pixel or several pixels of the transmission type spatial modulation element 57.

Figure 8:
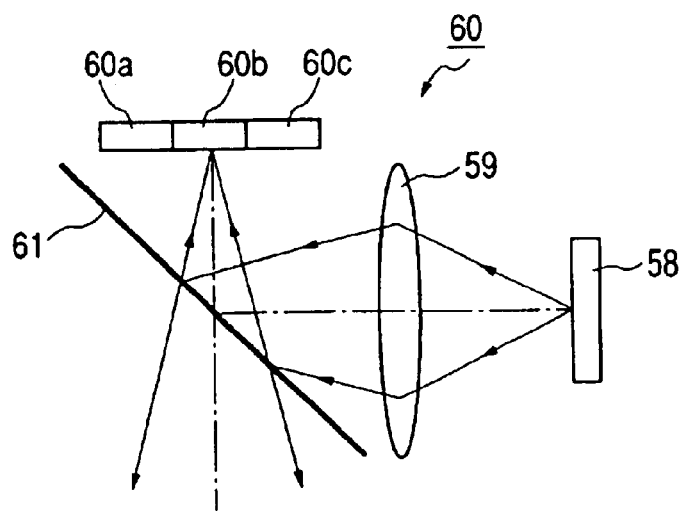
FIG. 8 is an explanatory diagram to illustrate the illumination means in the image observation apparatus of the present invention.

In FIG. 8, the illumination light source 11 is comprised of a surface emitting light source (surface illuminant) 58, a lens 59, a half mirror 61, and a reflection type spatial modulation element 60 such as a reflective liquid crystal panel or the like. A unit light source 51 is comprised of one pixel (60a, 60b, or 60c) or several pixels of the reflection type spatial modulation element 60. Here light from the surface emitting light source 58 is reflected by the half mirror 61 to enter the spatial modulation element 60. The light optically modulated by the spatial modulation element 60 travels through the half mirror 61 to illuminate the image display means (see FIG. 1).

Figure 9A:
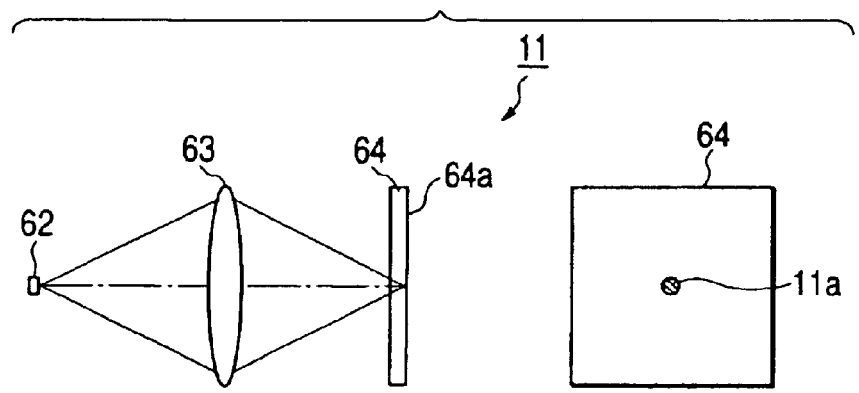
FIGS. 9A, 9B and 9C are explanatory diagrams to illustrate the illumination means in the image observation apparatus of the present invention.
Figure 9B:
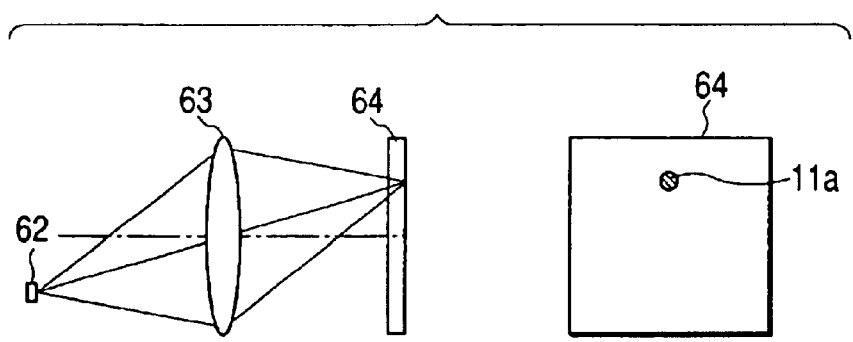
Figure 9C:
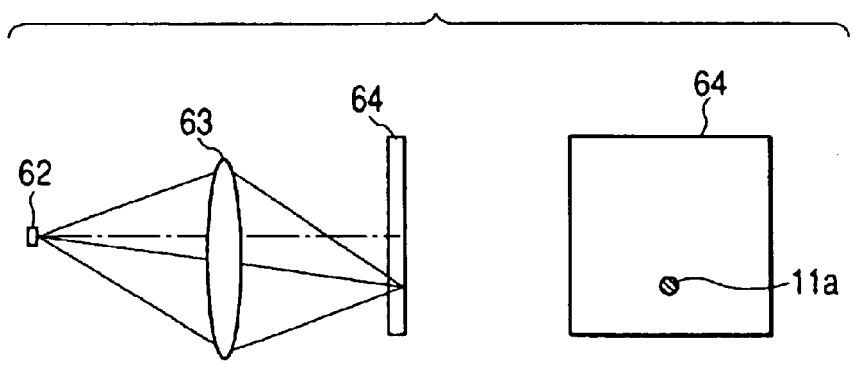

Another configuration of the illumination light source 11 can be realized by the structure illustrated in FIGS. 9A to 9C. A side view of main part is presented on the left side while a front view of main part on the right side in each figure. The illumination light source 11 has a light source 62, which can be regarded substantially as a point light source, an illumination lens 63 of a positive power, and a diffuser plate 64. As illustrated in FIG. 9A, when the light source 62 is placed in the conjugate relation with a diffusing surface 64a of the diffuser plate 64, the illumination light source 11 becomes a light source having a light-emitting surface 11a of a small area. As illustrated in FIGS. 9B and 9C, the position of the light-emitting surface 11a of the illumination light source 11 can be varied by moving the illumination lens 63 or the light source 62 in the direction normal to the optical axis.

A plurality of unit light sources in respective divided areas can be realized by the above configurations of the illumination light source 11. The shape of the unit sources does not always have to be rectangular as illustrated, but it can be any shape such as a circle, an ellipse, a polygon, and so on. The unit sources do not have to be arranged in the continuous array of unit sources as illustrated in FIG. 4, but they may also be arranged in a discrete pattern.

Each of embodiments of the image observation apparatus according to the present invention will be described below.
(Embodiment 1)

Figure 10:
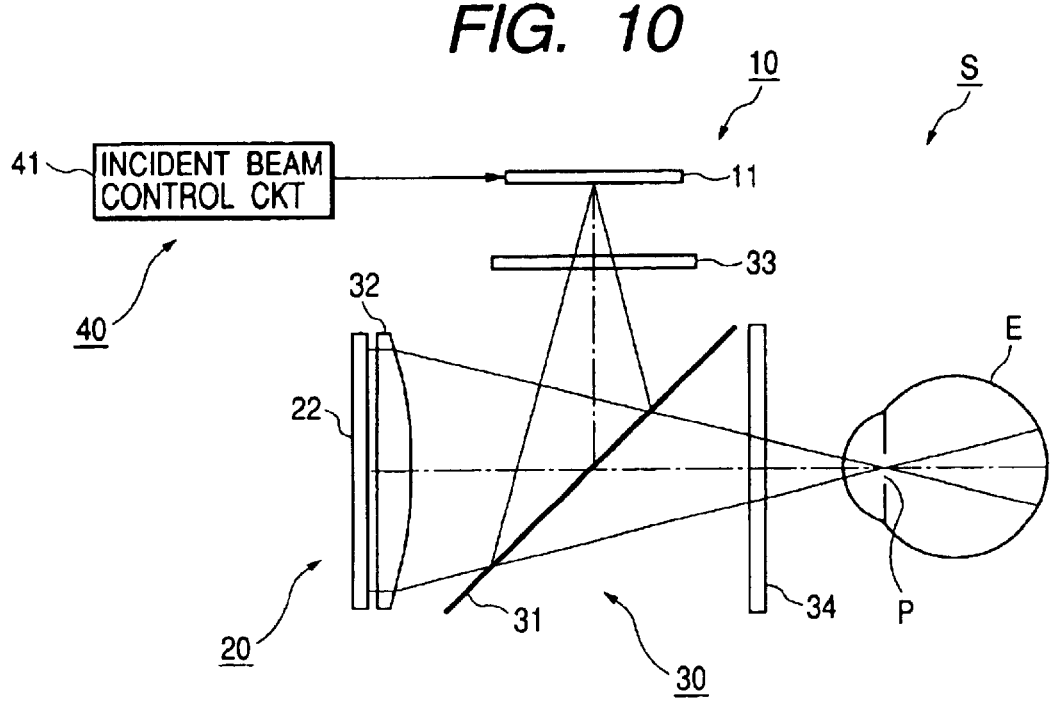
FIG. 10 is a schematic diagram to show the main part of Embodiment 1 of the image observation apparatus according to the present invention.

FIG. 10 is a schematic diagram to illustrate the main part of Embodiment 1 of the image observation apparatus according to the present invention. This apparatus is generally provided with the illumination means 10 having the illumination light source 11, the image display means 20 for displaying the image information, the display optical system 30 for focusing the image of the illumination light source 11 of the illumination means 10 at or near the position of the pupil P of the observing eye E and directly projecting the image information displayed on the image display means 20 under illumination with the light from the illumination means 10, onto the retina of the observing eye E, and the control means 40.

The light emitted from the illumination light source 11 of the illumination means 10 travels through a polarizer 33 to be converted into linearly polarized light. Part of the linearly polarized light is reflected by a half mirror 31 and then is guided to a lens 32 to be refracted thereby and guided to a display element 22 of the display means 20. The display element 22 is a reflection type display element such as a reflective liquid crystal panel having the pixel structure, which has, for example, a function of reflecting the linearly polarized light incident on pixels in "ON" display part while rotating the direction of polarization thereof by 90° but reflecting the linearly polarized light incident on pixels in "OFF" display part while preserving the direction of polarization thereof.

The light reflected by the display element 22 is again refracted by the lens 32 and part thereof is transmitted by the half mirror 31 to be guided to a polarizer 34. The polarizer 34 is placed so that the axis of transmitted polarization thereof is perpendicular to that of the polarizer 33. Since the reflected light from the pixels in the "ON" display part of the display element 22 has the direction of polarization rotated by 90°, it travels through the polarizer 34 to be guided to the observing eye E. However, since the reflected light from the pixels in the "OFF" display part of the display element 22 has the direction of polarization preserved, it is intercepted by the polarizer 34 and thus does not enter the observing eye E.

The display optical system 30 forms the image 11' of the illumination light source 11 at the position of the pupil P of the observing eye E. The size of the illumination light source 11, the position and focal length of the display optical system 30, etc. are set so that the size of the illumination light source image 11' at this time is sufficiently smaller than the pupil P of the observing eye E. The observer observes the image information displayed on the image display means 20 under illumination with the light from the illumination means 10.

The incident beam control circuit 41 controls the illumination means 10, based on the image information and the output from the pupil position detecting means described hereinafter, to change the position of the light-emitting surface of the illumination light source 11, thereby changing the position of the incident beam at the pupil position of the observing eye E.

The reflection type display element 22 does not always have to be a liquid crystal panel, but may be a micromirror device or the like. When the display element 22 is the micromirror device, there is no need for use of the polarizers 33, 34.

Figure 11:
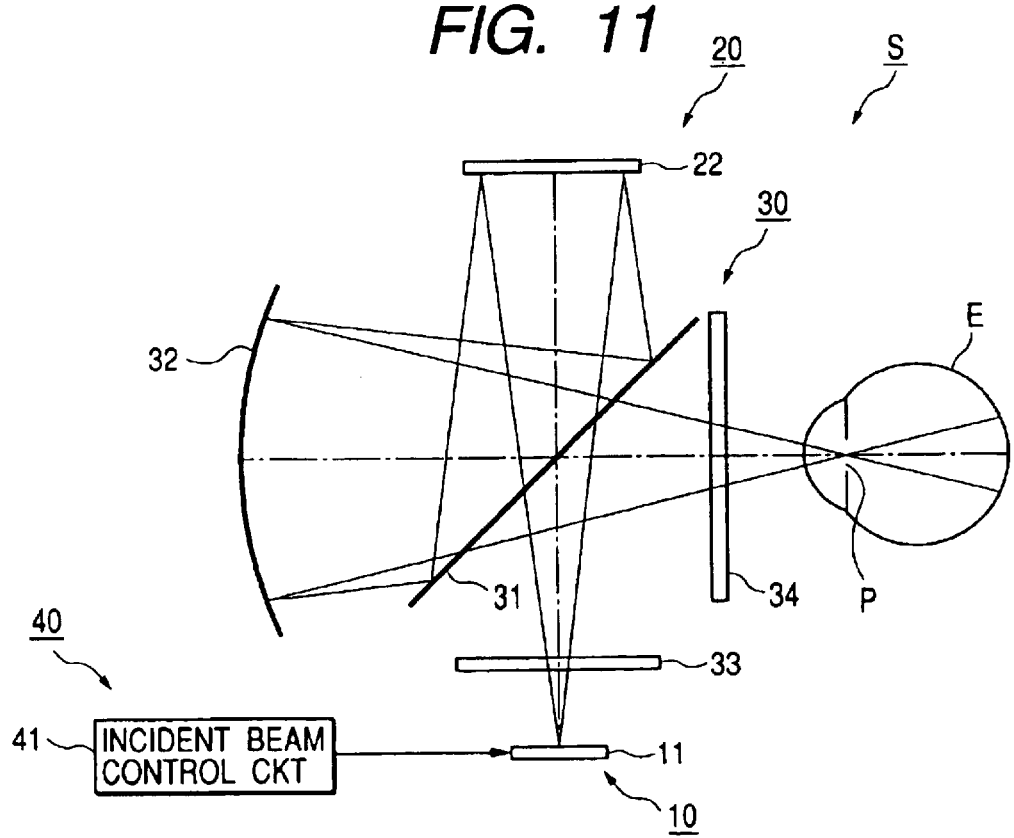
FIG. 11 is a schematic diagram to illustrate the main part of a modification with change in part of Embodiment 1 of the image observation apparatus according to the present invention.

The embodiment illustrated in FIG. 10 used the lens in the display optical system 30, but it may also be constructed using a reflector (concave mirror) having a curvature, such as a spherical surface, an aspherical surface, an ellipsoidal surface, a hyperboloidal surface, or the like, as illustrated in FIG. 11.

In FIG. 11, the elements having the same functions as those in the embodiment illustrated in FIG. 10 are denoted by the same reference symbols and the description thereof is omitted herein.

The light emitted from the illumination light source 11 of the illumination means 10 travels through the polarizer 33 to be converted into linearly polarized light, and part thereof is transmitted by the half mirror 31 to be guided to the display element 22 of the display means 20. The light reflected by the display element 22 is then reflected in part by the half mirror 31, is reflected by the concave mirror 32, and is transmitted in part again by the half mirror 31 to be guided to the polarizer 34. Just as in the embodiment illustrated in FIG. 10, the reflected light from the pixels in the "ON" display part of the display element 22 is guided to the observing eye E, while the reflected light from the pixels in the "OFF" display part of the display element 22 does not enter the observing eye E. Here the polarizers 33, 34 also have a function of intercepting light emerging from the illumination light source 11 and reflected toward the observing eye E by the half mirror 33 to prevent it from entering the observing eye E.

The incident beam control circuit 41 controls the illumination means 10, based on the image information and the output of the pupil position detecting means described hereinafter, to change the position of the light-emitting surface of the illumination light source 11, thereby changing the position of the incident beam at the pupil position of the observing eye E.

Figure 12:
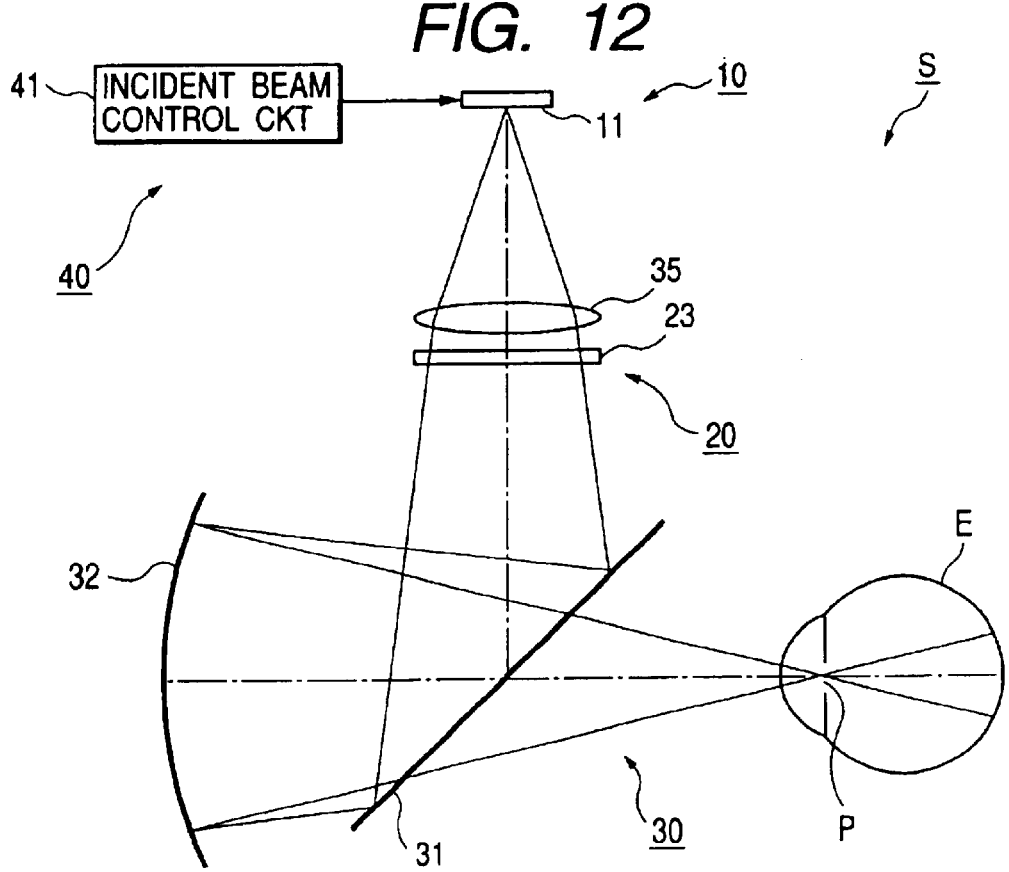
FIG. 12 is a schematic diagram to illustrate the main part of a modification with change in part of Embodiment 1 of the image observation apparatus according to the present invention.

In the embodiment illustrated in FIGS. 10, 11, the display element of the display means 20 was the reflection type display element (spatial modulation element), but the display element can be a transmission type display element (spatial modulation element) 23 as illustrated in FIG. 12.

In FIG. 12, the elements having the same functions as those in the embodiment illustrated in FIGS. 10 and 11 are denoted by the same reference symbols and the description thereof is omitted herein. The illumination light emitted from the illumination light source 11 of the illumination means 10 is refracted by a lens 35 to be guided to the display element 23 of the display means 20. The display element 23 is the transmission type display element consisting of polarizers, a transmissive liquid crystal panel, and so on. The light transmitted by the display element 23 is guided to the observing eye E by the display optical system 30 including the half mirror 31 and the concave mirror 32.

The incident beam control circuit 41 controls the illumination means 10, based on the image information and the output of the pupil position detecting means described hereinafter, to change the position of the light-emitting surface of the illumination light source 11, thereby changing the position of the incident beam at the pupil position of the observing eye E.

This construction permits the observer to observe a clear image of the image information on the display means 20 according to the principle illustrated in FIG. 1, FIG. 2, and FIG. 3, and the beam is incident to the eye without being intercepted even during the gaze at the marginal part of the field, thus enabling the display and observation in the wide angle of view.

(Embodiment 2)

Figure 13:
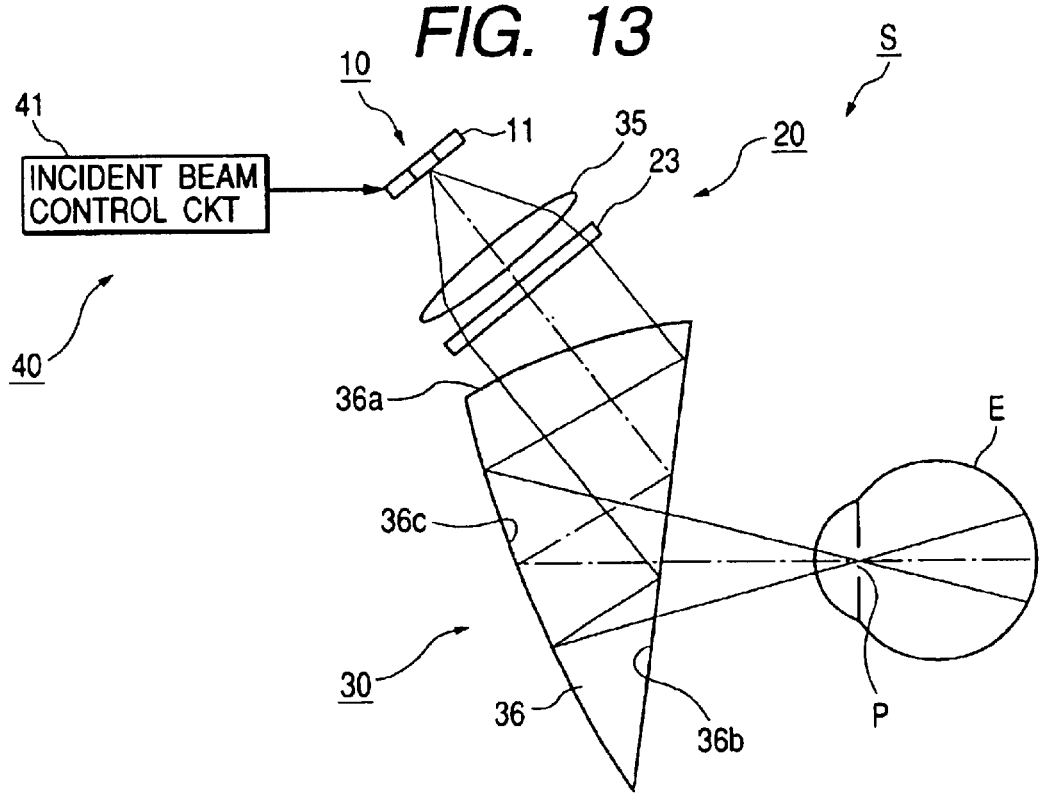
FIG. 13 is a schematic diagram to show the main part of Embodiment 2 of the image observation apparatus according to the present invention.

FIG. 13 is a schematic diagram to illustrate the major part of Embodiment 2 of the image observation apparatus according to the present invention. This apparatus, similar to the embodiment illustrated in FIG. 12, is generally provided with the illumination means 10 having the illumination light source 11, the image display means 20 for displaying the image information, the display optical system 30 for focusing the image of the illumination light source 11 of the illumination means 10 at or near the position of the pupil P of the observing eye E and directly projecting the image information displayed on the image display means 20 under illumination by the illumination means 10, onto the retina of the observing eye E, and the control means 40. The elements having the same functions as those in the embodiment illustrated in FIG. 12 are denoted by the same reference symbols and the description thereof is omitted herein.

The illumination light emitted from the illumination light source 11 of the illumination means 10 is refracted by the lens 35 to be guided to the display element 23 of the display means 20. The light transmitted through the display element 23 enters a prism body 36 while being refracted by a surface 36a thereof. The light entering the surface 36a of the prism body 36 is incident at an angle of incidence over the critical angle to a surface 36b to be totally internally reflected thereby. The light is then reflected by a mirror surface 36c and is incident at an angle of incidence below the critical angle this time to the surface 36b. Thus the light is refracted by the surface 36b to emerge from the prism body 36. Then the light is guided to the entrance pupil P of the observing eye E. The prism body 36 is configured to have at least one decentered, rotationally asymmetric surface with optical powers differing depending upon azimuth angles so as to well correct aberration caused by the tilted arrangement of its surfaces having their respective optical powers, thereby decreasing the size of the display optical system 30.

The incident beam control surface 41 controls the illumination means 10, based on the image information and the output of the pupil position detecting means described hereinafter, to change the position of the light-emitting surface of the illumination light source 11, thereby changing the position of the incident beam at the pupil position of the observing eye E.

Figure 14:
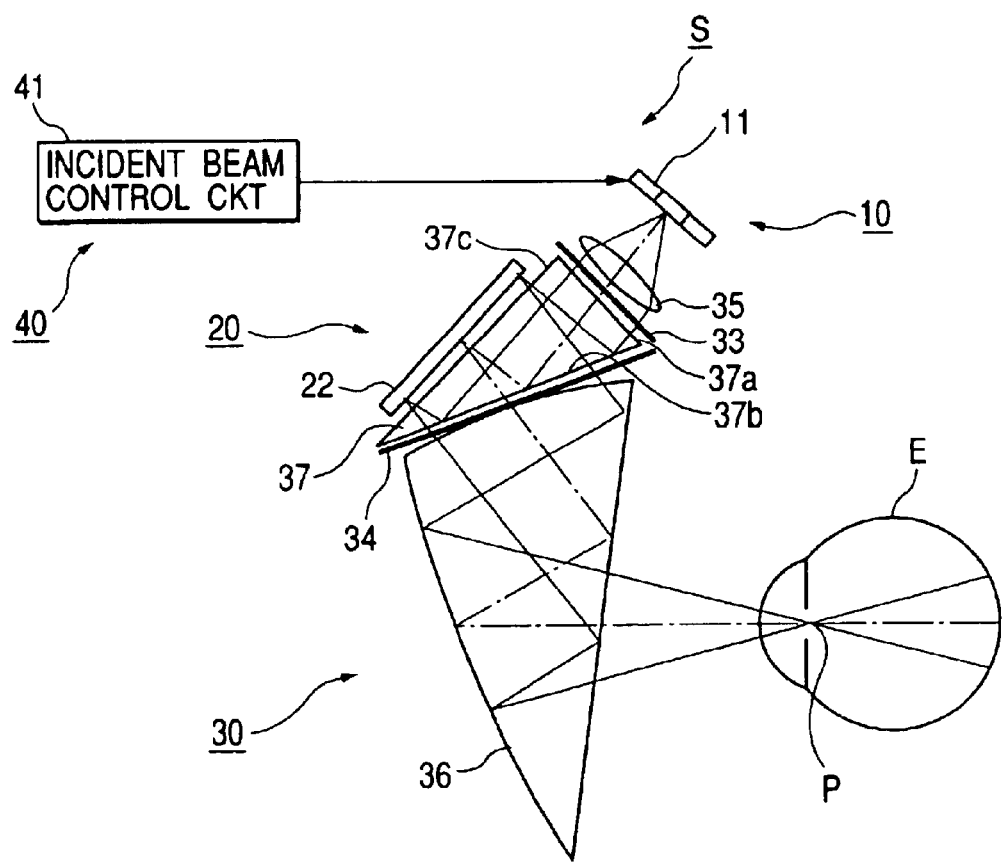
FIG. 14 is a schematic diagram to illustrate the main part of a modification with change in part of Embodiment 2 of the image observation apparatus according to the present invention.

In the embodiment illustrated in FIG. 13, the display element of the display means 20 can be replaced by a reflection type display element as illustrated in FIG. 14. The elements having the same functions as those in the embodiments illustrated in FIG. 11 and in FIG. 13 are denoted by the same reference symbols and the description thereof is omitted herein.

In FIG. 14, the illumination light emitted from the illumination light source 11 of the illumination means 10 is refracted by the lens 35 and travels through the polarizer 33 to be converted into linearly polarized light. The linearly polarized light enters a prism 37 while being refracted by a surface 37a thereof. The prism 37 is a triangular prism comprised of planes (which may also include a curved surface in part). The light entering the prism 37 is then incident at an angle over the critical angle to a surface 37b to be totally internally reflected thereby. Then the light emerges from the prism 37 while being refracted by a surface 37c thereof and is then incident to the reflective display element 22. The light reflected by the reflective display element 22 is incident to the prism 37 while being refracted by the surface 37c thereof. The light is again incident at an angle below the critical angle to the surface 37b and emerges from the prism 37 while being refracted thereby. The light is then incident to the polarizer 34. Just as in the embodiment illustrated in FIG. 11, the reflected light from the pixels in the "ON" display part of the display element 22 travels through the polarizer 34 and the reflected light from the pixels in the "OFF" display part of the display element 22 is intercepted by the polarizer 34. The light transmitted by the polarizer 34 is guided to the observing eye E while being reflected and refracted by the prism body 36 in the same manner as by that illustrated in FIG. 13. The size of the apparatus is decreased by constructing part of the display optical system 30 using the total internal reflection in the prism 37. In the present embodiment the surface 37b of the prism 37 was the total internal reflection surface, but it can also be a half mirror surface or a polarization beam splitter surface.

The incident beam control circuit 41 controls the illumination means 10, based on the image information and the output of the pupil position detecting means described hereinafter, to change the position of the light-emitting surface of the illumination light source 11, thereby changing the position of the incident beam at the pupil position of the observing eye E.

This construction permits the observer to observe a clear image of the image information of the display means 20 according to the principle illustrated in FIG. 1, FIG. 2, and FIG. 3, and enables the display and observation in the wide angle of view, because the beam is incident to the eye without being intercepted even during the gaze at the marginal part of the field.

(Embodiment 3)

Embodiment 3 of the image observation apparatus of the present invention will be described below.

There are known self-emission type display devices like EL panels. There are also known light-source-integrated display devices of integrated structure of a back light, polarizers, a transmissive liquid crystal panel, and so on. In the present embodiment the image observation apparatus is constructed using the self-emission type or light-source-integrated display device, as illustrated in FIG. 15.

Figure 15:
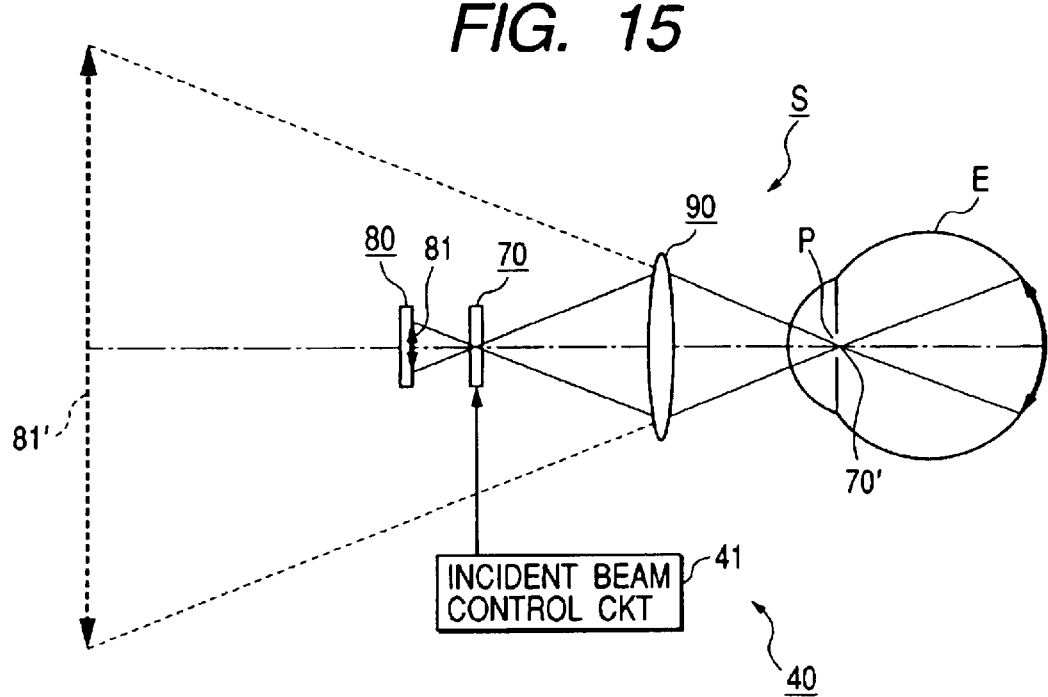
FIG. 15 is a schematic diagram to show the main part of Embodiment 3 of the image observation apparatus according to the present invention.

FIG. 15 is a schematic diagram to show the main part of Embodiment 3 of the image observation apparatus according to the present invention.

The image observation apparatus S according to the present invention has a self-emission type image display means 80 such as an EL panel for displaying the image information 81, a display optical system (eyepiece optical system) 90, a spatial modulation element 70, and the control means 40.

In FIG. 15, the light emitted from the image display means 80 travels through the spatial modulation element 70 and is guided to the observing eye E by the display optical system 90. The observer observes an image 81' formed by the display optical system 90 from the image information 81 displayed on the image display means 80.

The display optical system 90 forms an image 70' of the spatial modulation element 70 at the position of the pupil P of the observing eye. This permits the state of the incident beam at the position of the entrance pupil of the observer to be changed by controlling positions of transmitting and intercepting portions of the spatial modulation element 70.

The incident beam control circuit 41 controls the positions of the transmitting and intercepting portions of the spatial modulation element 70, based on the image information and the output of the pupil position detecting means described hereinafter, to change the position of the incident beam at the pupil position of the observing eye E.

This construction permits the observer to observe a clear image of the image information of the display means 80 in the manner similar to the principle illustrated in FIG. 1, FIG. 2, and FIG. 3, and enables the display and observation in the wide angle of view, because the beam is incident to the eye without being intercepted even during the gaze at the marginal part of the field.

(Embodiment 4)

Figure 16:
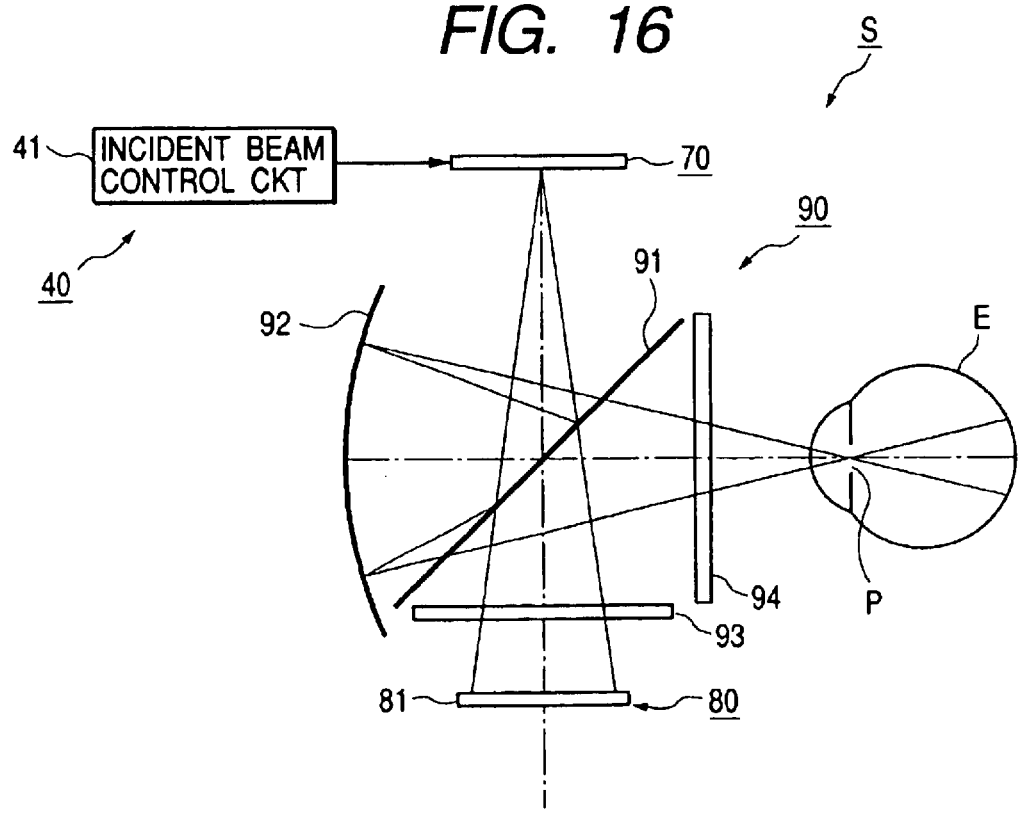
FIG. 16 is a schematic diagram to show the main part of Embodiment 4 of the image observation apparatus according to the present invention.

FIG. 16 is a schematic diagram to show the main part of Embodiment 4 of the image observation apparatus according to the present invention. This apparatus has the self-emission type image display means 80 for displaying the image information, the spatial modulation element 70, the display optical system 90 for guiding the image information to the observing eye E, and the control means 40.

The light emitted from the image information 81 displayed on the image display means 80 travels through a polarizer 93 to be converted into linearly polarized light. Part of the linearly polarized light is transmitted by a half mirror 91 to be guided to the spatial modulation element 70. The spatial modulation element 70 is a reflection type spatial modulation element such as a reflective liquid crystal panel having the pixel structure, which has, for example, the function of reflecting the linearly polarized light incident on the pixels in "ON" part while rotating the direction of polarization thereof by 90° but reflecting the linearly polarized light incident on the pixels in "OFF" part while preserving the direction of polarization thereof.

The light reflected by the spatial modulation element 70 is reflected in part by the half mirror 91 and is then reflected by a concave mirror 92 having a curvature. Part of the reflected light is transmitted by the half mirror 91 again to be guided to a polarizer 94. The polarizer 94 is placed so that its axis of transmitted polarization is perpendicular to that of the polarizer 93. Since the reflected light from the pixels in the "ON" part of the spatial modulation element 70 has the direction of polarization rotated by 90°, it is transmitted through the polarizer 94 to be guided to the observing eye E. However, since the reflected light from the pixels in the "OFF" part of the spatial modulation element 70 has the direction of polarization preserved, it is intercepted by the polarizer 94 so as not to enter the observing eye E. The polarizer 94 also have the function of intercepting the light emitted from the image display means 80, transmitted through the polarizer 93, and reflected in part toward the observing eye E by the half mirror 91 so as to prevent it from entering the observing eye E.

The display optical system 90 forms the image 70' of the spatial modulation element 70 at the position of the pupil P of the observing eye. This permits the state of the incident beam at the entrance pupil position of the observer to be changed by controlling the positions of the transmitting and intercepting portions of the spatial modulation element 70.

The incident beam control circuit 41 controls the positions of the transmitting and intercepting portions of the spatial modulation element 70, based on the image information and the output of the pupil position detecting means described hereinafter, to change the position of the incident beam at the pupil position of the observing eye E.

Figure 17:
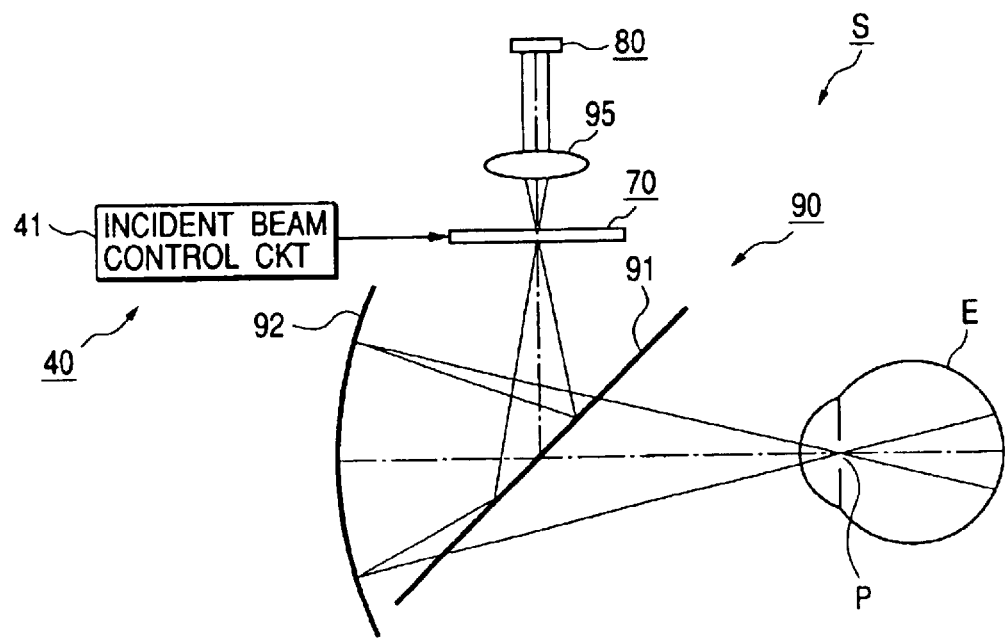
FIG. 17 is a schematic diagram to illustrate the main part of a modification with change in part of Embodiment 4 of the image observation apparatus according to the present invention.

In the embodiment illustrated in FIG. 16, the spatial modulation element 70 was the reflection type element, but a transmission type spatial modulation element may also be used as illustrated in FIG. 17.

In FIG. 17, the elements having the same functions as those in the embodiment illustrated in FIG. 16 are denoted by the same reference symbols and the description thereof is omitted herein. The light emitted from the image display device 80 is guided to the spatial modulation element 70 while being refracted by a lens 95. The spatial modulation element 70 is the transmission type spatial modulation element comprised of polarizers, a transmissive liquid crystal panel, and so on. The light transmitted through the spatial modulation element 70 is guided to the observing eye E by the display optical system 90 consisting of the half mirror 91 and the concave mirror 92. The display optical system 90 forms the image 70' of the spatial modulation element 70 at the position of the pupil P of the observing eye E.

The incident beam control circuit 41 controls the positions of the transmitting and intercepting portions of the spatial modulation element 70, based on the image information and the output of the pupil position detecting means described hereinafter, to change the position of the incident beam at the pupil position of the observing eye E.

This construction permits the observer to observe a clear image in the manner similar to the principle illustrated in FIG. 1, FIG. 2, and FIG. 3, and enables the display and observation in the wide angle of view, because the beam is incident without being intercepted even during the gaze at the marginal part of the field.

Figure 18:
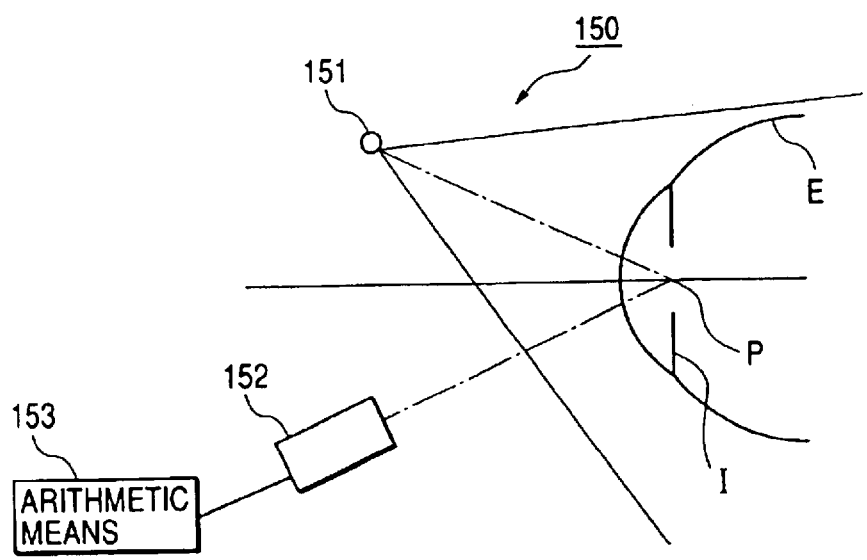
FIG. 18 is an explanatory diagram to illustrate the pupil position detecting means of the image observation apparatus of the present invention.
Figure 19A:
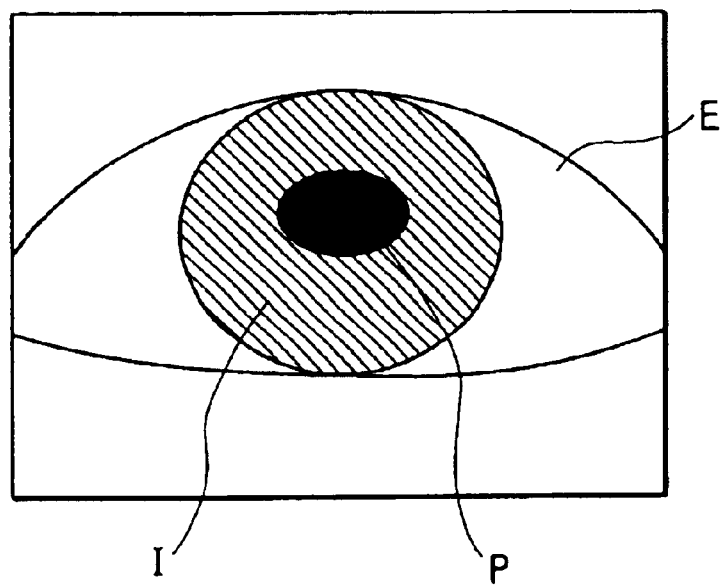
FIGS. 19A and 19B are explanatory diagrams to illustrate detection of pupil position in the image observation apparatus of the present invention.
Figure 19B:
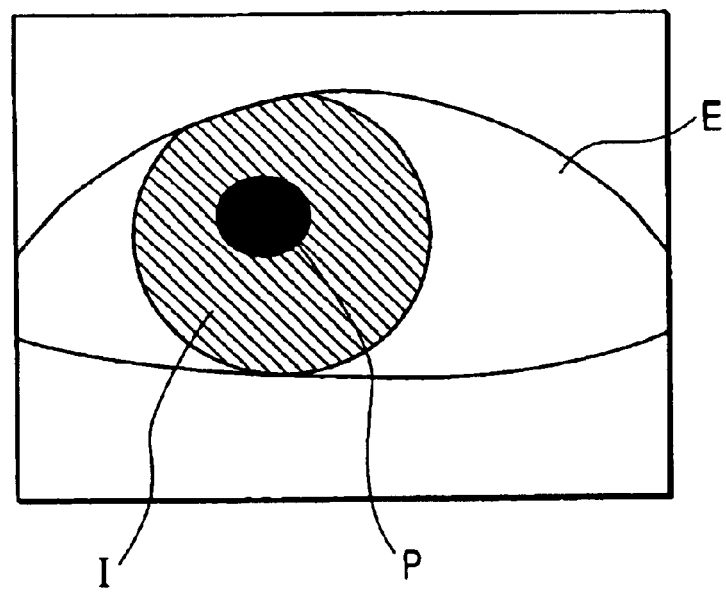

FIG. 18 and FIGS. 19A, 19B show a specific configuration of the pupil position detecting system (pupil position detecting means) used in each embodiment. In FIG. 18 the pupil position detecting system 150 has an eyeball illuminating means 151, a light receiving means 152 for receiving reflected light by the observing eye E from the illumination light emitted from the eyeball illuminating means 151, and an arithmetic means 153. The pupil position detecting system 150 is located at a position where the system does not interfere with the optical paths and the like of the display optical system for observation of the image, for example, at a position in the vertical direction in the case of FIG. 18. The eyeball illuminating means 151 is an infrared LED or the like. Use of infrared light permits the pupil position to be detected without affecting the observation of image.

The light receiving means 152 is composed of a lens and an image pickup device such as a CCD or the like. FIGS. 19A and 19B show images of the observing eye E received by the light receiving means 152. Intensities of reflected light from respective portions of the observing eye E become weaker in the order of skin of palpebra and the like, sclera, iris I, and pupil P. Therefore, the arithmetic means 153 extracts the darkest portion in the received image and calculates the position of the center thereof to detect the pupil position. FIG. 19A shows a situation in which the observer is gazing at the central part of the field, and FIG. 19B a situation in which the observer is gazing at the marginal part of the field (or looking aside).

The method of detecting the pupil position can be a method of detection using reflected light from the retina, and the light receiving element can be one selected from a line sensor, a PSD, a quatrefoil sensor, and so on.

Figure 20A:
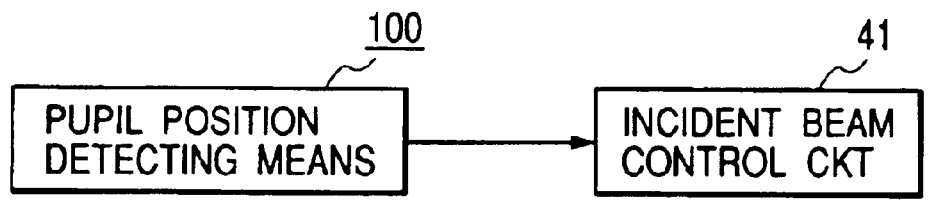
FIGS. 20A and 20B are explanatory diagrams to illustrate an input signal into an incident beam control circuit in the image observation apparatus of the present invention.
Figure 20B:
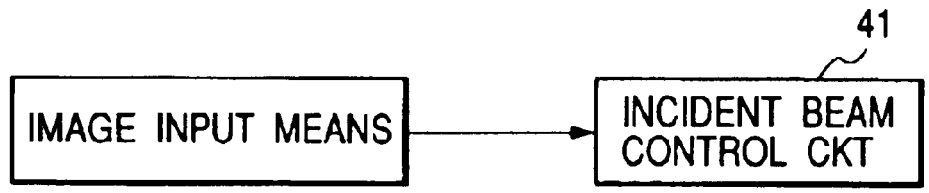

The pupil position detecting means 150 sends the information of the detected pupil position to the incident beam control means 41, as illustrated in FIG. 20A, and the incident beam control means 41 controls the illumination means 10 or the spatial modulation element 70, based on the information, as described in each of the embodiments described above. In another configuration, as illustrated in FIG. 20B, the control means can also be configured to automatically determine the direction of the visual axis of the observer, e.g., from the position of an image including a high-frequency component in the screen, based on the image information from the image input means, calculate an estimated pupil position, and control the illumination means 10 or the spatial modulation element 70, based thereon.

Figure 36:
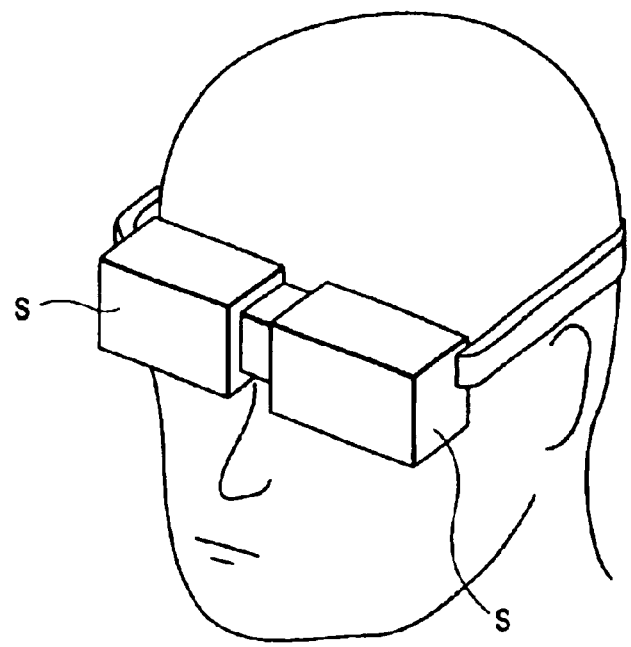
FIG. 36 is an explanatory diagram to illustrate an image observation system of the present invention.
Figure 37:
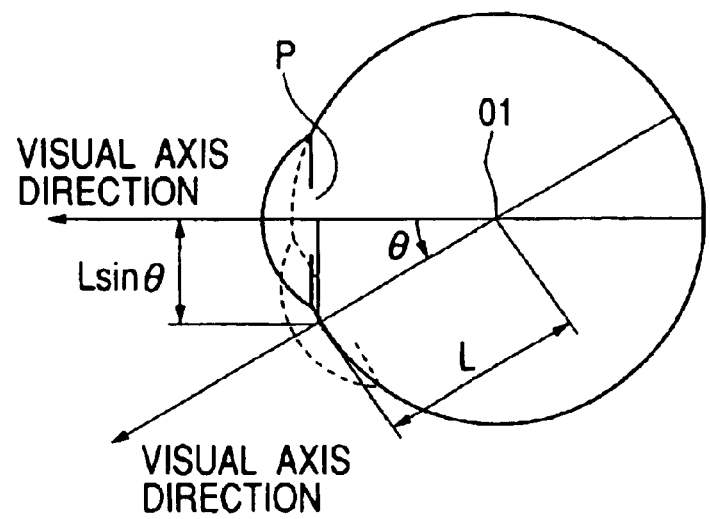
FIG. 37 is an explanatory diagram to illustrate the relation between the observing eye of the observer and the range of field.
Figure 38A:
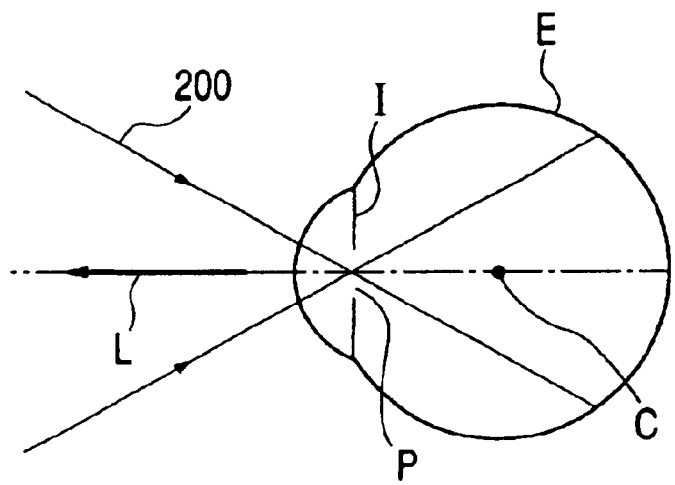
FIGS. 38A and 38B are explanatory diagrams to show the relation between the observing eye of the observer and the range of the field.
Figure 38B:
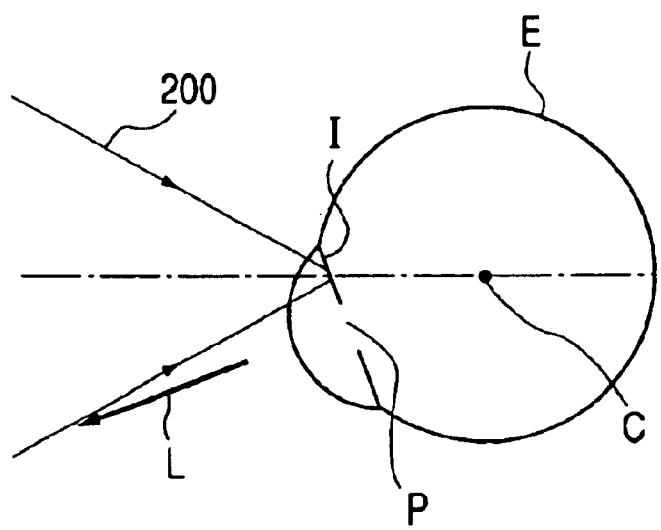

Further, when a pair of image observation devices S as described in each of the above embodiments are provided for the left and right eyes of the observer as illustrated in FIG. 36, it becomes feasible to implement the stereoscopic vision using the binocular parallax and to provide an image observation system such as a head-mounted display or the like being capable of reducing the contradiction between convergence and accommodation of the observing eyes, which can occur during observation of the stereoscopic image by use of only the binocular parallax, because the focus states of the observed images are independent of the accommodation of the eyes, and thus permitting the observer to observe the stereoscopic image well in the natural state. In particular, since the beam is incident on the eye without being intercepted even during the gaze at the marginal part of the field in the construction using the image observation apparatus of the present invention, it becomes feasible to implement the display and observation in the wide angle of view and reproduce the space in the wide range in the depth direction.

According to the present invention, as described above, during the observation of the image information displayed on the image display means the beam is incident on the eyeball without being intercepted by the iris even during the gaze at the marginal part of the field with rotation of the eyeball from the center of the field whereby it becomes feasible to implement the display and observation in the wide angle of view and whereby the space can be reproduced in the wide range in the depth direction during the observation of the stereoscopic image. Therefore, the present invention can accomplish the image observation apparatus and the image observation systems using the apparatus.

FIG. 21 to FIG. 24 are explanatory diagrams to illustrate the basic concept in further embodiments of the image observation apparatus of the present invention. The image observation apparatus S according to the present invention is generally provided with the illumination means 10 having the illumination light source 11 comprised of a plurality of unit light sources, the image display means 20 for displaying the image information 21 including parallax images, the display optical system 30, and the control means 40.

Figure 21:
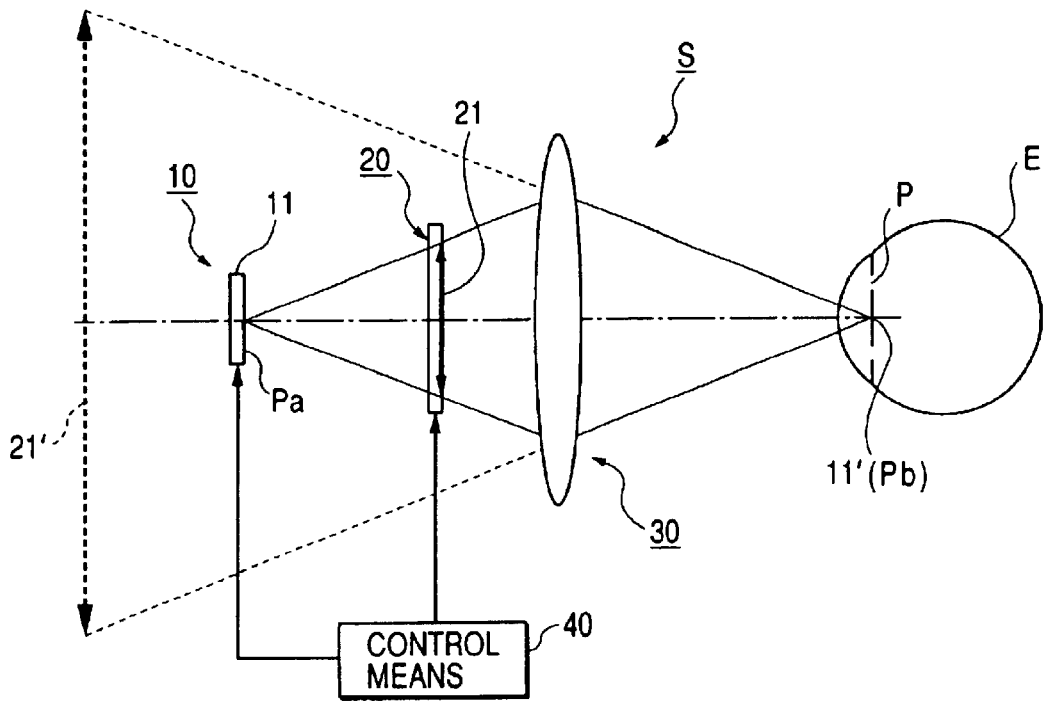
FIG. 21 is an explanatory diagram to illustrate the basic concept of the optical system in the image observation apparatus according to a further aspect of the present invention.

In FIG. 21, the illumination means 10 is located at or near the position Pa of the entrance pupil of the display optical system 30 and the display optical system 30 forms the image 11' of the illumination light source 11 at the position of the exit pupil Pb of the display optical system 30 being in the conjugate relation with the entrance pupil Pa.

The observer substantially aligns the entrance pupil P of the eye E with the exit pupil Pb of the display optical system 30 (to such an extent that the observer can observe the image, which also applies to the following), whereby the observer observes the image (enlarged virtual image) 21' formed by the display optical system 30 from the image information 21 displayed on the image display means 20 under illumination by the illumination means 10. The position, the focal length, etc. of the display optical system 30 are determined so that the enlarged virtual image of the display element surface of the image display means 20 is focused, for example, 2 m ahead of the eye E.

Figure 22:
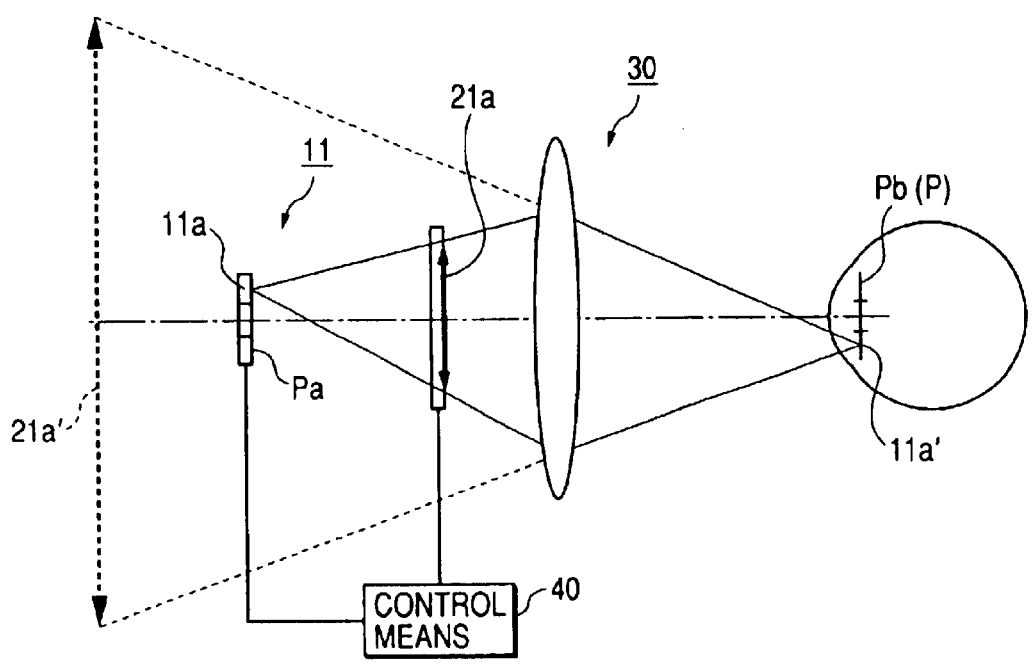
FIG. 22 is an explanatory diagram to illustrate the basic concept of the optical system in the image observation apparatus according to the further aspect of the present invention.
Figure 23:
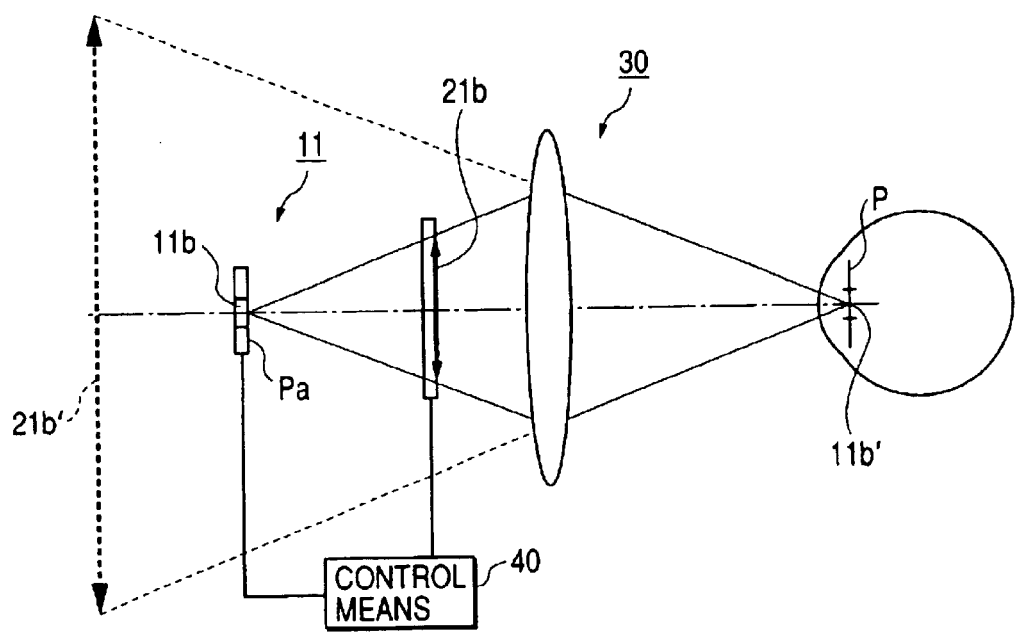
FIG. 23 is an explanatory diagram to illustrate the basic concept of the optical system in the image observation apparatus according to the further aspect of the present invention.
Figure 24:
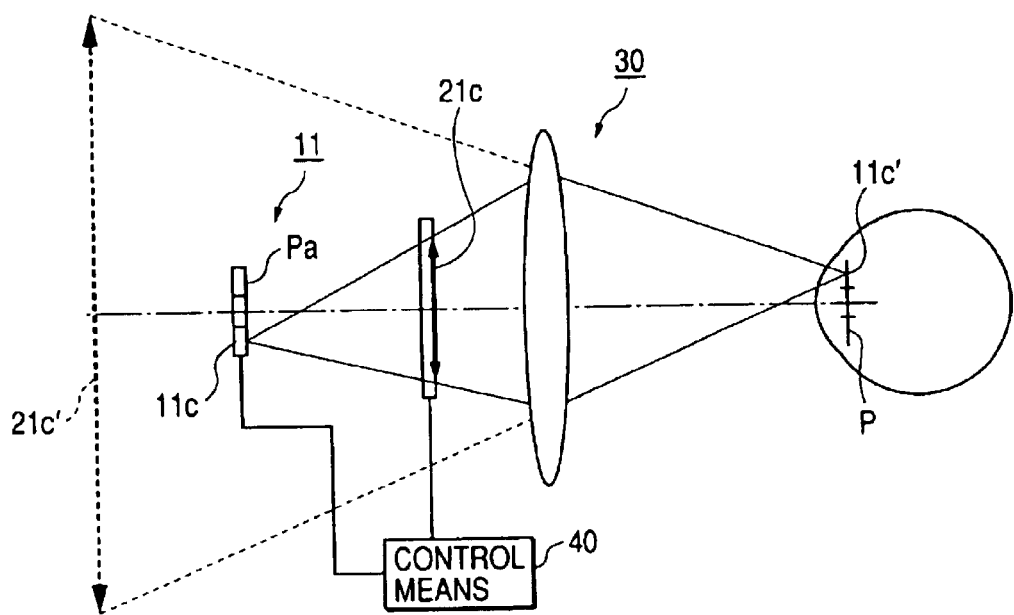
FIG. 24 is an explanatory diagram to illustrate the basic concept of the optical system in the image observation apparatus according to the further aspect of the present invention.

A method of sequentially injecting a plurality of parallax images into a single eye E will be described below with reference to FIGS. 22 to 24. FIGS. 22 to 24 are top plan views of the image observation apparatus S according to the present invention. FIGS. 22 to 24 show a case for displaying three parallax images in the horizontal direction for simplicity, but it is noted that the number of parallax images is not limited to this number and that an arbitrary number of parallax images can be injected based on the display view angle, resolving power, and so on, including a plurality of parallax images in the vertical direction. For example, the apparatus may be constructed in a structure to inject totally twelve parallax images, i.e., four parallax images horizontal by three parallax images vertical.

The illumination light source 11 is composed of a plurality of unit light sources 11$a$, 11$b$, 11$c$, which are sequentially lighted up (in time series) by the control means 40, as illustrated in FIGS. 22 to 24. An image of each light source 11$a$ to 11$c$ is formed in each area 11$a'$ to 11$c'$ of the exit pupil Pb. This results in spatially dividing the exit pupil Pb of the display optical system 30 into a plurality of regions (11$a'$, 11$b'$, 11$c'$), and it thus becomes feasible to control the beam incident on each region 11$a'$ to 11$c'$ in time division. At this time the control means 40 switches the image information 21 displayed on the image display means 20 among parallax image information pieces 21$a$, 21$b$, 21$c$ in response to the above switching of the unit light sources. The image information pieces 21$a$, 21$b$, 21$c$ are small parallax images obtained (or observed) when the view point is located at the position of the center of each region 11$a'$, 11$b'$, 11$c'$ on the pupil plane P to view the reproduced object. Since the switching operations of the light source 11 and the image information 21 synchronized therewith by the control means 40 are repeatedly carried out in shorter periods than the permissible time of persistence of vision for the observer's eye, the switching operations can be performed without being perceived by the observer.

Figure 25A:
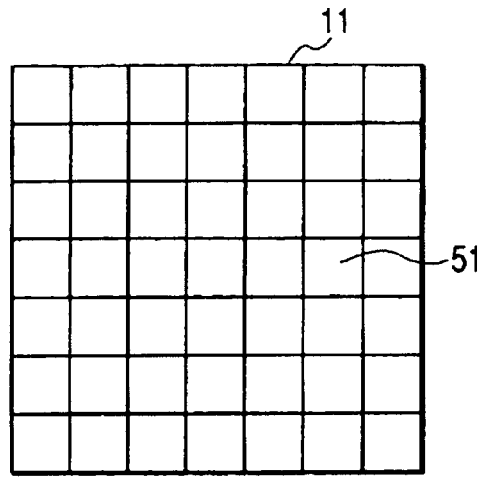
FIGS. 25A, 25B and 25C are explanatory diagrams to illustrate the illumination means of the image observation apparatus according to the present invention.

The illumination light source 11 consisting of the plurality of unit light sources 11$a$ to 11$c$ of the illumination means 10 has the structure as illustrated in FIG. 25A. As illustrated in FIG. 25A, the illumination light source 11 is composed of a plurality of unit light sources 51 resulting from region-based division of the total area. FIG. 25A shows a case in which the size of the exit pupil Pb of the display optical system is, for example, 10.5 mm×10.5 mm and intervals between centers of segmental regions in the entrance pupil P of the observing eye E are 1.5 mm, in consideration of the display view angle, resolving power, and so on, and thus there are totally forty nine parallax images, i.e., seven parallax images horizontal by seven parallax images vertical. The unit light sources 51 correspond to the unit light sources 11$a$, 11$b$, 11$c$ in FIG. 22 to FIG. 24. In the conventional image observation apparatus, it was necessary to repeatedly carry out the operation of sequentially lighting up all the forty nine unit sources 51 and switching the parallax images displayed on the image display means 20 in synchronism therewith in the periods shorter than the permissible time of persistence of vision for eye. When the display view angle is small and thus the number of parallax images to be presented to the observing eye is small, there is no need for use of the image display means operating at so high speed. However, the image display means operating at very high speed had to be used in order to display the forty nine parallax images as illustrated in FIG. 25A, in the periods shorter than the permissible time of persistence of vision for eye.

Figure 25B:
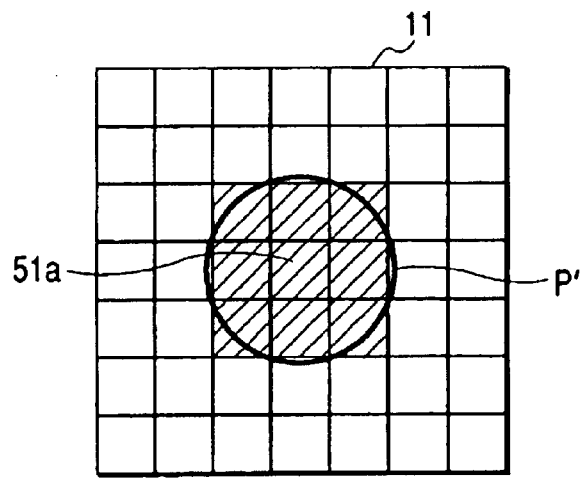
Figure 25C:
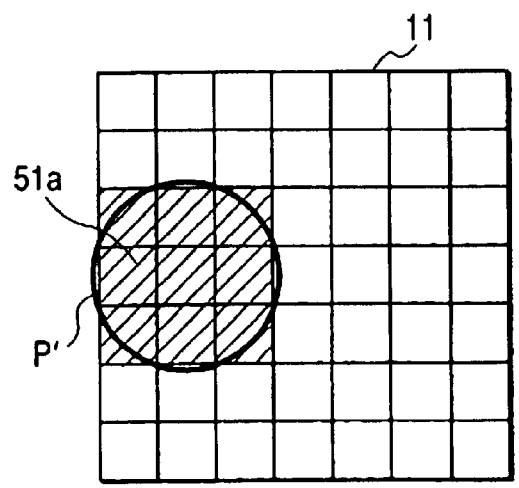

In the image observation apparatus according to the present invention, the control means 40 does not light all the plurality of unit light sources 51 constituting the illumination light source 11 in time division, but selectively lights unit light sources according to the pupil position of the observing eye E, based on the displayed image information and the information from the pupil position detecting means described hereinafter. This will be described referring to FIGS. 25B and 25C. FIGS. 25B and 25C show the illumination light source 11 and in the figures P' represents a projected image at the position of the illumination light source 11 by the display optical system 30 from the pupil P of the observing eye E.

For example, when the observer is gazing at the central part of the field as illustrated in FIG. 25B, the control means successively lights up only nine unit sources 51$a$ (hatched in the figure) corresponding to the position and size of the projected image P' of the pupil P and displays parallax images corresponding to the positions of the respective unit sources in the image display means 20 in synchronism therewith. When the observer is gazing at the marginal part of the field as illustrated in FIG. 25C, similarly, the control unit also successively lights up only nine unit sources 51$a$ (hatched in the figure) corresponding to the position of the projected image P' of the pupil P and displays parallax images corresponding to the positions of the respective unit sources in the image display means 20 in synchronism therewith.

In the structure as described above, the number of parallax images displayed on the image display means 20 is always nine and is greatly decreased, thus permitting construction of the image observation apparatus of the wide field angle without need for use of the very quick image display means.

In the example illustrated in FIGS. 25A to 25C, the illumination light source is composed of the forty nine unit light sources from the beginning and they are selectively and successively lighted up, but the illumination light source can also be constructed in such structure that it is composed of nine unit light sources of 3×3 and the illumination light source itself is mechanically moved in correspondence to the position of the pupil P of the observing eye E.

Figure 26A:
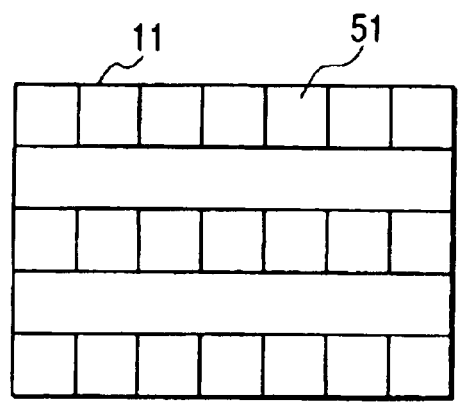
FIGS. 26A, 26B and 26C are explanatory diagrams to illustrate the illumination means of the image observation apparatus according to the present invention.
Figure 26B:
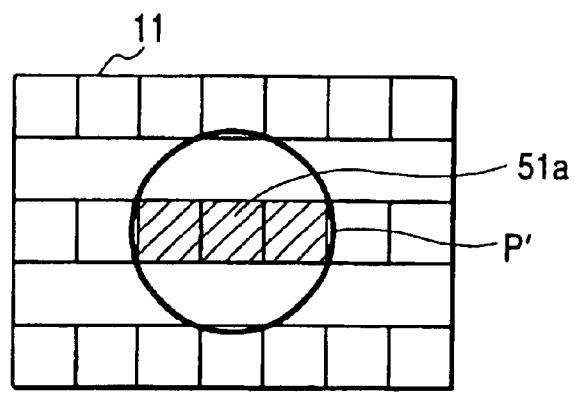

Further, since influence of parallax in the horizontal direction is stronger than that in the vertical direction in the stereoscopic vision, it becomes feasible to further decrease the number of parallax images to be displayed, by setting the number of parallax images in the vertical direction smaller than the number of parallax images in the horizontal direction. For example, FIG. 26A shows a configuration in which the number of unit light sources 51 making the illumination light source 11 is 21 in total, 7 horizontal and 3 vertical, which can also achieve a like effect even in the number smaller than that in the configuration illustrated in FIG. 25A. The control means 40 selectively lights the unit light sources corresponding to the position of the projected image P' of the pupil P of the observer in the same manner as in the method illustrated in FIGS. 25B and 25C, to present parallax images to the observing eye.

Figure 26C:
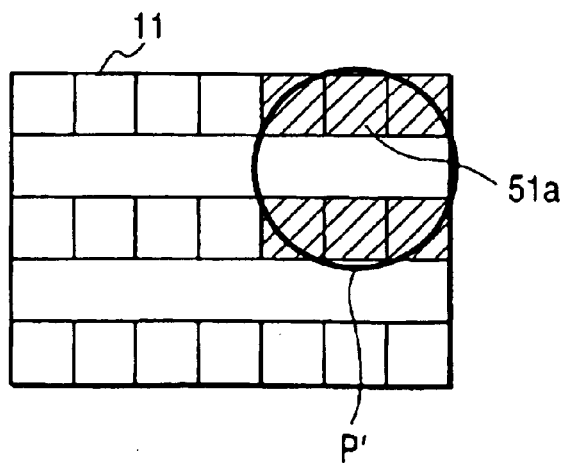

It is noted that all the unit light sources 51a corresponding to the position of the projected image of the pupil P on the illumination light source 11 do not have to be lighted up and an arbitrary number of unit light sources may be further selected and lighted up out of the unit light sources corresponding to the pupil position to be presented to the observing eye. In an example, in FIG. 26C, there are six unit light sources 51a corresponding to the position of the projected image P' of the observer's pupil P, and only three out of them are selectively successively lighted up. In a further example, in FIGS. 25B and 25C, six unit light sources are selectively and successively lighted up. These configurations can simplify the structure of the apparatus, because the number of parallax images to be displayed is fixed regardless of the pupil position of the observing eye.

In FIG. 25B, the size of the exit pupil of the display optical system is one enough to cover all the illumination light source 11, the unit light sources to be lighted are only in the portion of 51a corresponding to the size of the entrance pupil of the observing eye, and the size of the beam from the image display means at the position of the entrance pupil of the observing eye illuminated by the light source is equal to or smaller than the size of the entrance pupil of the observing eye.

As described above, the size of the exit pupil of the display optical system is set larger than the pupil of the observing eye and only the display beam corresponding to the pupil position of the observing eye is generated by control of the light source as illustrated in FIGS. 25A to 25C and FIGS. 26A to 26C, whereby the size of the beam from the image display means at the position of the entrance pupil P of the observing eye becomes substantially equal to or smaller than the size of the entrance pupil P of the observing eye, thus enabling the stereoscopic display of the "super-multiview regions" in the wide angle of view without need for use of the very quick image display means.

Figure 27A:
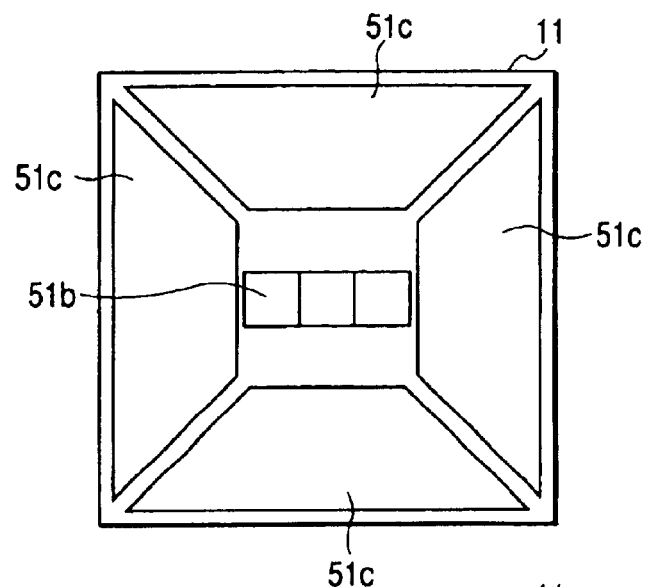
FIGS. 27A, 27B and 27C are explanatory diagrams to illustrate the illumination means of the image observation apparatus according to the present invention.
Figure 27B:
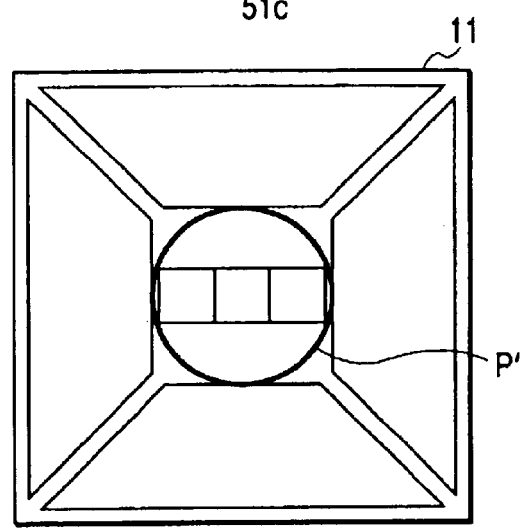
Figure 27C:
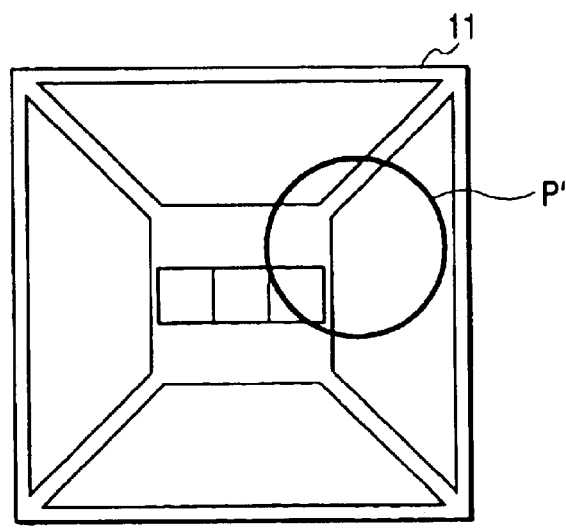

It is also feasible to implement the display and observation in the wide angle of view when the illumination light source 11 in the present embodiment is replaced by that of the configuration illustrated in FIG. 27A. As illustrated in FIG. 27A, the area of each of the four unit light sources 51c in the outermost periphery region constituting the illumination light source 11 is set wider than that of each of the unit light sources 51b other than those in the outermost periphery region. The control means successively lights up the unit light sources 51b, 51c (totally seven sources in the example illustrated in FIG. 27A) and displays the parallax images corresponding to the positions of the respective unit light sources in the image display means in synchronism therewith. This construction permits the observer to observe the image with the display beam entering the pupil P of the observing eye E, regardless of where the observer is gazing in the field, as illustrated in FIGS. 27B and 27C, without need for setting the number of parallax images to be presented to the observing eye, to a large value, and thus enables the stereoscopic display of the "super-multiview regions" in the wide angle of view without need for use of the very quick image display means.

As described above, the present embodiment is arranged to spatially divide the exit pupil of the display optical system into the plurality of regions, cause the plurality of parallax images corresponding to the positions of the respective regions to be incident on the observing eye so as to guide the plurality of parallax images into the single eye of the observer, and set the area of the regions in the outermost periphery among the plurality of regions of the exit pupil to be larger than the area of the regions except for the regions in the outermost periphery, thereby permitting the observation of the stereoscopic image in good order.

The illumination light source 11 is comprised of a light-emitting element array such as an EL panel or an LED array, or constructed in either of the structures as illustrated in FIGS. 5 to 8.

Embodiments of the image observation apparatus of the present invention will be detailed below.

(Embodiment 5)

Figure 28:
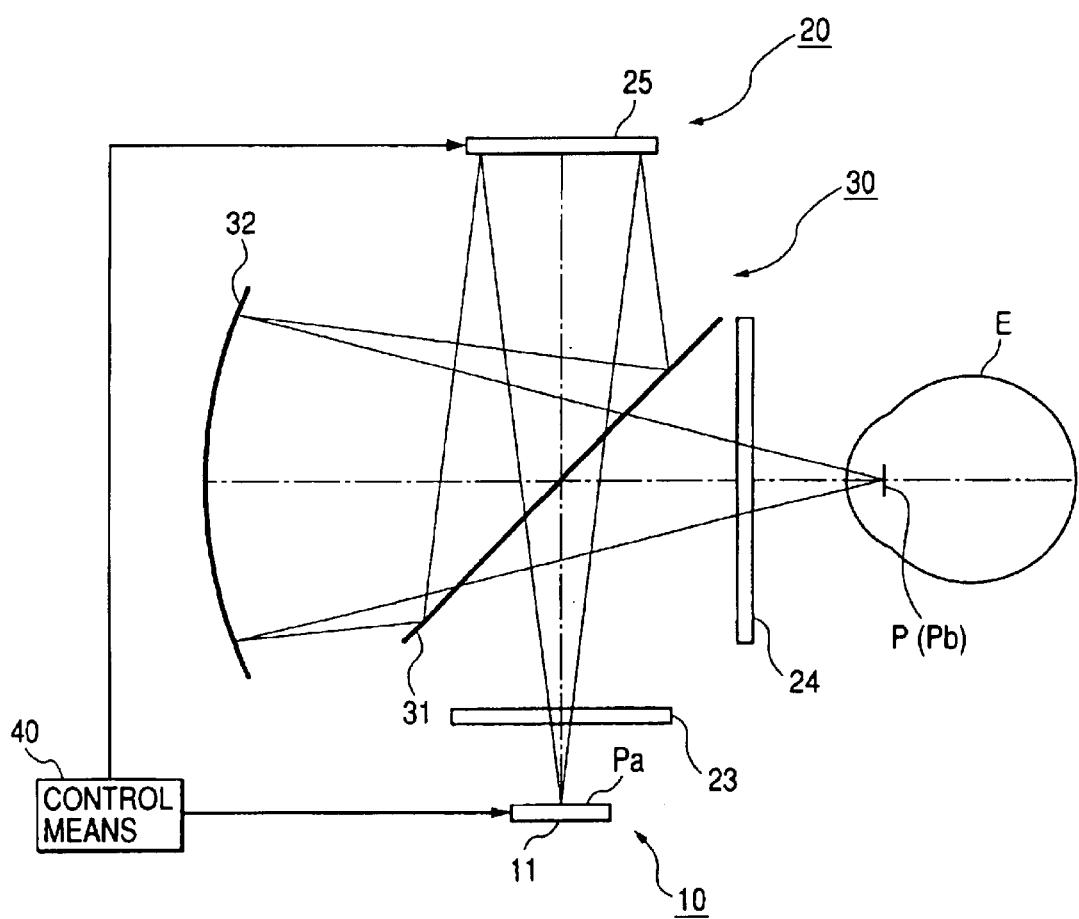
FIG. 28 is a schematic diagram to show the main part of Embodiment 5 of the image observation apparatus according to the present invention.

FIG. 28 is a schematic diagram to illustrate the main part of Embodiment 5 of the image observation apparatus according to the present invention. This apparatus is generally provided with the illumination means 10 having the illumination light source 11 consisting of a plurality of unit light sources, the image display means 20 for displaying the image information, the display optical system 30 for guiding the image information displayed on the image display means 20 under illumination with the light from the illumination means 10, to the observing eye E, and the control means 40.

The light emitted from the plurality of unit light sources of the illumination means 10 travels through the polarizer 23 to be converted into linearly polarized light. Part of the linearly polarized light is transmitted through the half mirror 31 to be guided to the display element 25. The display element 25 is a reflection type display element such as a reflective liquid crystal panel having the pixel structure or the like, which has, for example, the function of reflecting the linearly polarized light incident on the pixels in the "ON" display part while rotating the direction of polarization thereof by 90° but reflecting the linearly polarized light incident on the pixels in the "OFF" display part while preserving the direction of polarization thereof.

The light reflected by the display element 25 is reflected in part by the half mirror 31 and the reflected light is reflected by the concave mirror 32 having a curvature, such as a spherical surface, an aspherical surface, an ellipsoidal surface, a hyperboloidal surface, or the like. The light is transmitted in part through the half mirror 31 to be guided to the polarizer 24. The polarizer 24 is arranged so that the axis of transmitted polarization thereof is perpendicular to that of the polarizer 23. The reflected light from the pixels in the "ON" display part of the display element 25 is transmitted by the polarizer 24 to be guided to the observing eye E, because the direction of polarization thereof is rotated by 90°. However, the reflected light from the pixels in the "OFF" display part of the display element 25 is not incident on the observing eye E while being intercepted by the polarizer 24, because the direction of polarization thereof is preserved. The polarizer 24 also has the function of intercepting the light emitted from the illumination light source 11, transmitted through the polarizer 23, and reflected in part toward the observing eye E by the half mirror 31, so as to prevent it from entering the observing eye E.

The illumination light source 11 is located at or near the position Pa of the entrance pupil of the display optical system 30 and the display optical system 30 forms an image of the illumination light source 11 at or near the exit pupil Pb of the display optical system 30 being in the conjugate relation with the entrance pupil. The observer approximately aligns the entrance pupil P of the eye with the exit pupil Pb of the display optical system 30 whereby the observer observes the image formed by the display optical system 30 from the image information displayed on the image display means 20 under illumination by the illumination light source 11. The position, the focal length, etc. of the display optical system 30 are determined so that it forms an enlarged virtual image of the display element surface of the image display means 20, for example, 2 m ahead of the entrance pupil P.

The control means 40 performs control to appropriately switch the illumination light source 11 and the display element 25 in time division to cause a plurality of parallax images to be incident on the single eye of the observer, based on the principle illustrated in FIGS. 21 to 24, 25A to 25C, 26A to 26C and 27A to 27C, thereby enabling the stereoscopic display of the "super-multiview regions" in the wide angle of view.

Figure 29:
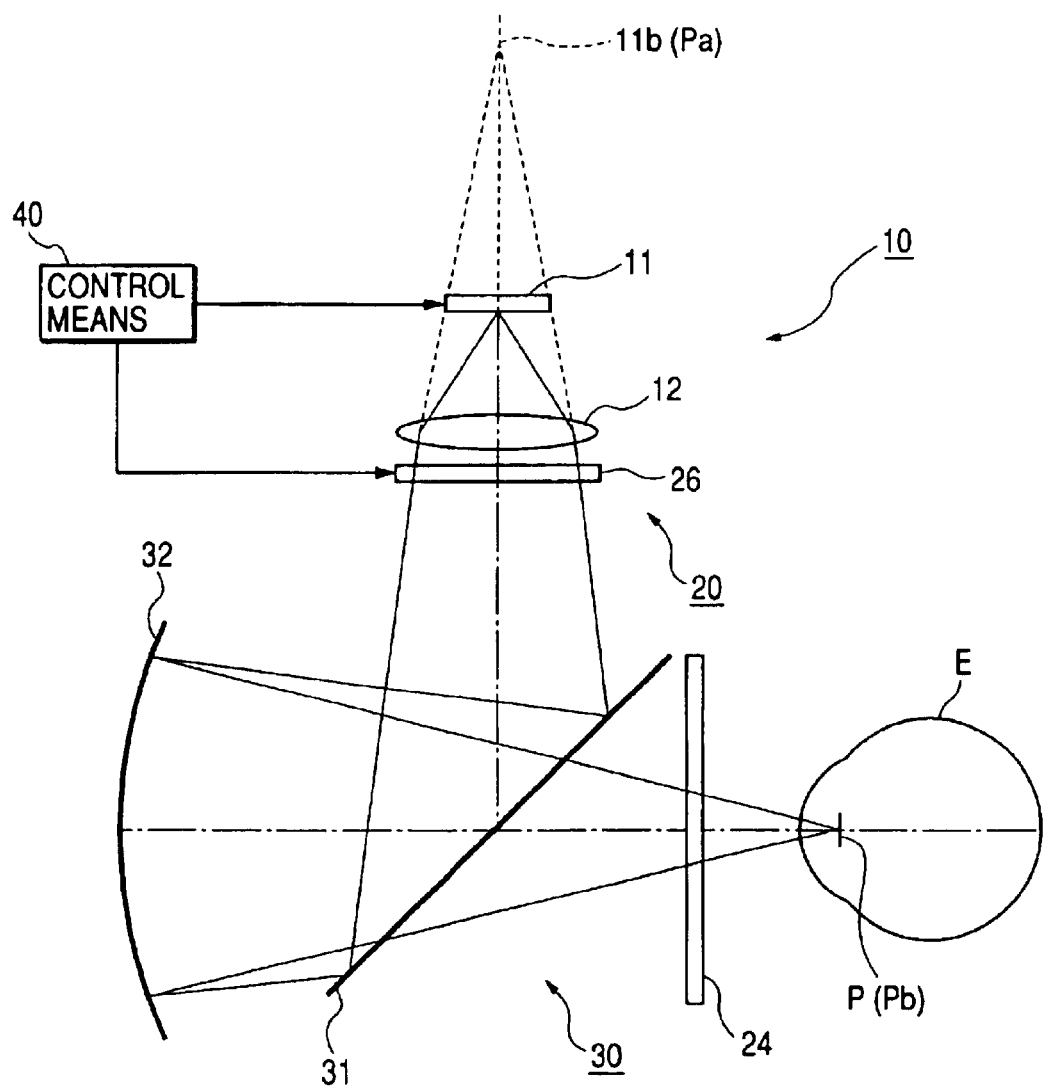
FIG. 29 is a schematic diagram to illustrate the main part with change in part of Embodiment 5 of the image observation apparatus according to the present invention.

The embodiment illustrated in FIG. 28 used the reflection type display element (spatial modulation element) as the display element of the display means 20, but the transmission type display element (spatial modulation element) 26 can also be employed as illustrated in FIG. 29.

In FIG. 29, the elements having the same functions as those in the embodiment illustrated in FIG. 28 are denoted by the same reference symbols and the description thereof is omitted herein. The illumination light emitted from the illumination light source 11 of the illumination means 10 is refracted by a condenser lens 12 to be guided to the display element 26 of the display means 20. The display element 26 is a transmission type display element composed of polarizers, a transmissive liquid crystal panel, and so on. The light transmitted through the display element 26 is guided to the observing eye E by the display optical system 30 consisting of the half mirror 31 and the concave mirror 32. The focal length, the position, etc. of the condenser lens 12 are determined so that the position 11b of the image of the illumination light source 11 by the condenser lens 12 is coincident with the position Pa of the entrance pupil of the display optical system 30. The display optical system 30 forms the image of the illumination light source 11 at the position of the exit pupil Pb thereof. The observer substantially aligns the entrance pupil P of the eye with the exit pupil Pb of the display optical system 30 whereby the observer observes the image formed by the display optical system 30 from the image information displayed on the image display means 20 under illumination by the illumination light source 11.

The control means 40 performs the control to properly switch the illumination light source 11 and the display element 26 in time division, so as to cause a plurality of parallax images to be incident on the single eye of the observer, based on the principle illustrated in FIGS. 21 to 24, 25A to 25C, 26A to 26C and 27A to 27C, thereby enabling the stereoscopic display of the "super-multiview regions" in the wide angle of view.

(Embodiment 6)

Figure 30:
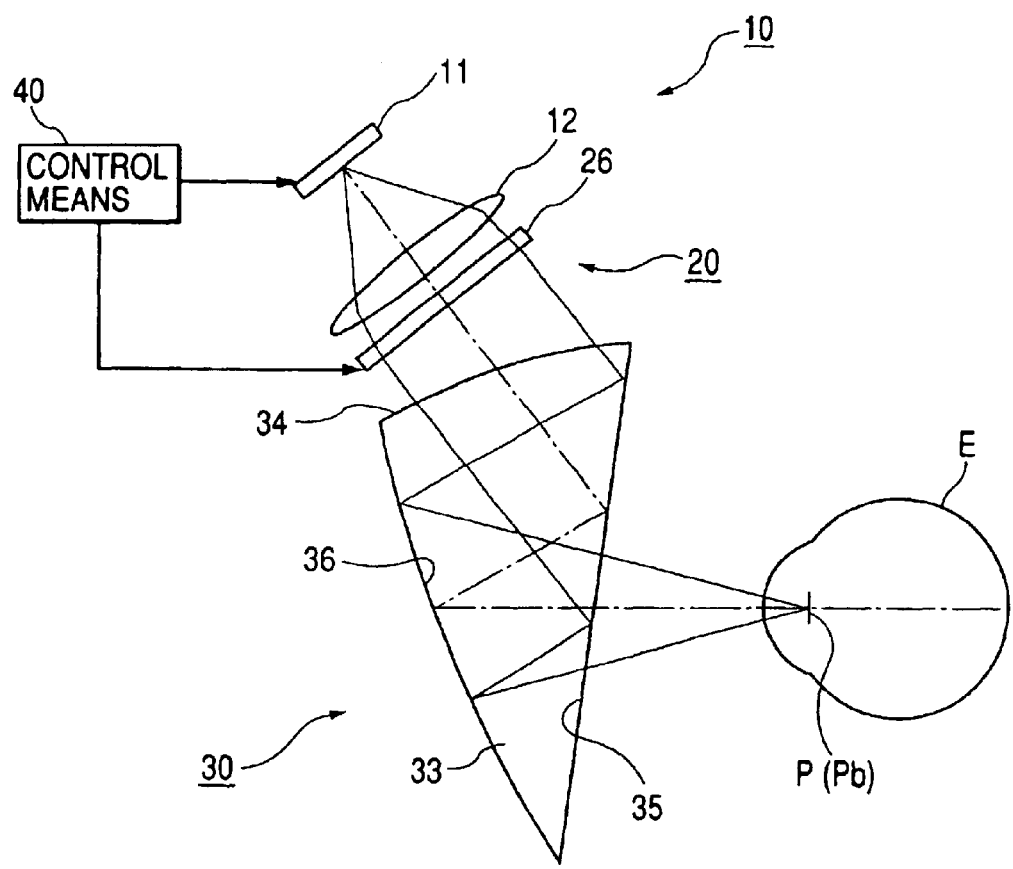
FIG. 30 is a schematic diagram to show the main part of Embodiment 6 of the image observation apparatus according to the present invention.

FIG. 30 is a schematic diagram to illustrate the main part of Embodiment 6 of the image observation apparatus according to the present invention. Just as in the embodiment illustrated in FIG. 29, this apparatus is generally provided with the illumination means 10 having the illumination light source 11 consisting of a plurality of unit light sources, the image display means 20 for displaying the image information, the display optical system 30 for guiding the image information displayed on the image display means 20 under illumination by the illumination means 10, to the observing eye E, and the control means 40. The elements having the same functions as those in the embodiment illustrated in FIG. 29 are denoted by the same reference symbols and the description thereof is omitted herein.

The illumination light emitted from the plurality of illumination light sources 11 in the illumination means 10 is refracted by the condenser lens 12 to be guided to the display element 26 of the display means 20. The light transmitted through the display element 26 is incident to a prism body 33 while being refracted by a surface 34 thereof. The light entering the prism body 33 is incident at an angle of incidence over the critical angle on a surface 35 thereof to be totally internally reflected thereby. The light is then reflected by a mirror surface 36 and is again incident at an angle of incidence below the critical angle on the surface 35 to emerge from the prism body 33 while being refracted thereby. The emerging light is guided to the entrance pupil P of the observing eye E. The prism body 33 is configured so as to have at least one decentered, rotationally asymmetric surface with optical powers differing depending upon azimuth angles in order to well correct the aberration caused by the tilted arrangement of the surfaces having their respective optical powers, thereby decreasing the size of the display optical system 30. The position, the focal length, etc. of the prism body 33 are determined so that it forms an enlarged virtual image of the display element surface of the display means 20, for example, 2 m ahead of the entrance pupil P.

The display optical system 30 forms the image of the illumination light source 11 at the position Pb of the exit pupil thereof. The observer substantially aligns the entrance pupil P of the eye with the exit pupil Pb of the display optical system 30 whereby the observer observes the image formed by the display optical system 30 from the image information displayed on the image display means 20 under illumination by the illumination light source 11.

The control means 40 performs the control to properly switch the illumination light source 11 and the display element 26 in time division, so as to cause a plurality of parallax images to be incident on the single eye of the observer, based on the principle illustrated in FIGS. 21 to 24, 25A to 25C, 26A to 26C and 27A to 27C, thereby enabling the stereoscopic display of the "super-multiview regions" in the wide angle of view.

Figure 31:
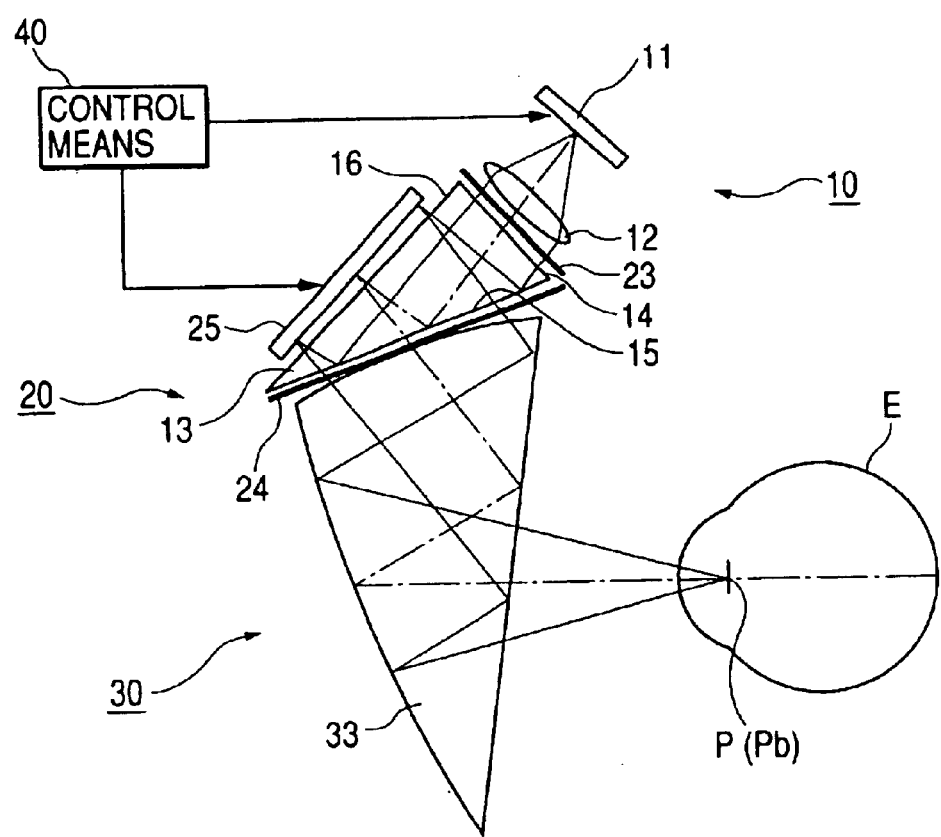
FIG. 31 is a schematic diagram to illustrate the main part of a modification with change in part of Embodiment 6 of the image observation apparatus according to the present invention.

In the embodiment illustrated in FIG. 30, the display element of the display means 20 can be a reflection type display element as illustrated in FIG. 31. The elements having the same functions as those in the embodiments illustrated in FIG. 28 and FIG. 30 are denoted by the same reference symbols and the description thereof is omitted herein.

In FIG. 31, the illumination light emitted from the illumination light source 11 of the illumination means 10 is refracted by the condenser lens 12 and travels through the polarizer 23 to be converted into linearly polarized light. The linearly polarized light is incident to a prism 13 while being refracted by a surface 14 thereof. The prism 13 is a triangular prism composed of planes (which may include a curved surface in part). The light entering the prism 13 is incident at an angle over the critical angle on a surface 15 to be totally internally reflected thereby. The reflected light is then refracted by a surface 16 to emerge from the prism 13. The emerging light is incident to the reflection type display element 25. The light reflected by the reflection type display element 25 is incident to the prism 13 while being refracted by the surface 16 thereof. Then the light is again incident at an angle below the critical angle to the surface 15 to emerge from the prism 13 while being refracted thereby. The emerging light is then incident to the polarizer 24. Just as in the embodiment illustrated in FIG. 28, the reflected light from the pixels in the "ON" display part of the display element 25 is transmitted through the polarizer 24, while the reflected light from the pixels in the "OFF" display part of the display element 25 is intercepted by the polarizer 24. The light transmitted through the polarizer 24 is guided to the observing eye E while being reflected and refracted in the same manner as described in FIG. 30, by the prism body 33. The size of the apparatus is decreased by constructing the illumination means 10 by use of the total internal reflection in the prism 13. In the present embodiment the surface 15 of the prism 33 is the total internal reflection surface, but it may also be a half mirror surface or a polarization beam splitter surface.

The display optical system 30 forms the image of the illumination light source 11 at the position Pb of the exit pupil thereof. The observer substantially aligns the entrance pupil P of the eye with the exit pupil of the display optical system 30 whereby the observer observes the image formed by the display optical system 30 from the image information displayed on the image display means 20 under illumination by the illumination light source 11.

The control means 40 performs the control to properly switch the illumination light source 11 and the display element 25 in time division, so as to cause a plurality of parallax images to be incident on the single eye of the observer, based on the principle illustrated in FIGS. 21 to 24, 25A to 25C, 26A to 26C and 27A to 27C, thereby enabling the stereoscopic display of the "super-multiview regions" in the wide angle of view.

In the embodiments illustrated in FIG. 28 to FIG. 31, the illumination light source and display element were controlled by time-division switching at high speed in order to cause the plurality of parallax images to be incident on the observing eye, but a like effect can also be attained by provision of a plurality of display means.

(Embodiment 7)

Figure 32:
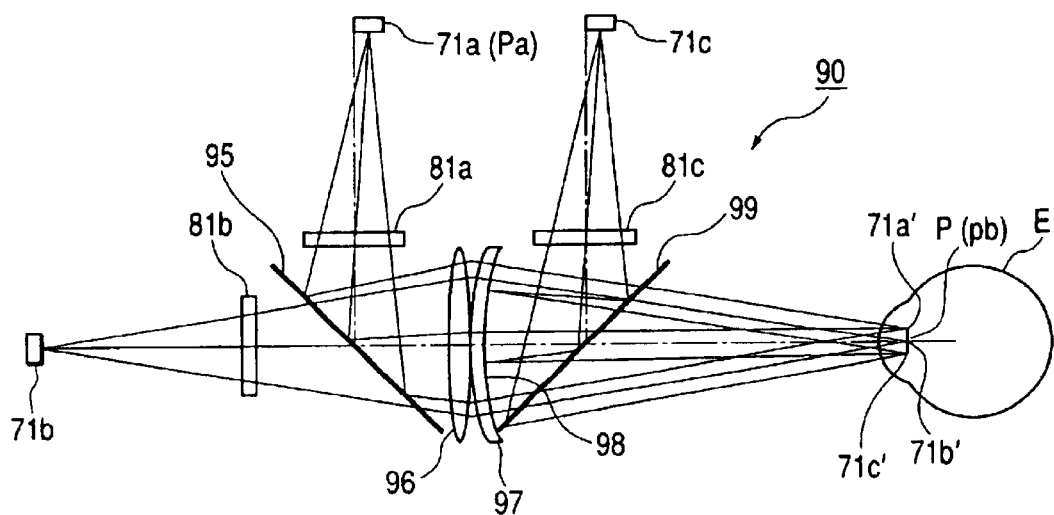
FIG. 32 is a schematic diagram to show the main part of Embodiment 7 of the image observation apparatus according to the present invention.

FIG. 32 is a schematic diagram to show the main part of Embodiment 7 of the image observation apparatus of the present invention. This apparatus has a plurality of illumination light sources 71a, 71b, 71c, a plurality of display means 81a, 81b, 81c corresponding to the respective illumination light sources, and the display optical system 90.

The light emitted from the illumination light source 71a travels through the transmission type display element 81a and is reflected in part by a half mirror 95. The reflected light travels while being converged by optical elements 96, 97, and part thereof is transmitted through a half mirror 99 to be guided to the observing eye E. A half mirror coat is laid on one surface 98 forming the optical element 97. The light emitted from the illumination light source 71b travels through the transmission type display element 81b and part thereof is transmitted through the half mirror 95. Just as in the case of the light from the illumination light source 71a, the transmitted light travels through the optical elements 96, 97 and through the half mirror 99 to the observing eye E. The light emitted from the illumination light source 71c travels through the transmission type display element 81c and part thereof is reflected by the half mirror 99. The reflected light is reflected and converged by the half mirror surface 98 having a positive optical power and is transmitted by the half mirror 99 again, to be guided to the observing eye E. The illumination light source 71a is located at or near the position Pa of the entrance pupil of the display optical system 90 and the display optical system 90 forms an image 71a' of the illumination light source 71a on or near the exit pupil Pb thereof. Likewise, the light emitted from the illumination light source 71b, 71c illuminates the corresponding transmission type display element 81b, 81c and the display optical system 90 forms the image 71b', 71c' on the exit pupil thereof.

The observer substantially aligns the entrance pupil P of the eye with the exit pupil of the display optical system 90 whereby the observer observes the image formed by the display optical system 90 from the image information displayed on the transmission type display element 81a, 81b, 81c under illumination by the illumination light source 71a, 71b, 71c. The position, the focal length, etc. of the display optical system 90 are determined so that it forms enlarged virtual images of the display element surfaces of the transmission type display elements 81a, 81b, 81c, for example, 2 m ahead of the entrance pupil P.

The transmission type display elements 81a, 81b, 81c display parallax images corresponding to the respective images 71a', 71b', 71c' of the illumination light sources.

As described above, the apparatus of the present embodiment is provided with a plurality of display means to cause a plurality of parallax images to be incident on the single eye of the observer without use of quick image display means, thereby enabling the stereoscopic display of the "super-multiview regions."

In the embodiment illustrated in FIG. 32, a method for display of color image can be either selected from a method of constructing the illumination light sources 71a, 71b, 71c of white light sources and the display elements 81a, 81b, 81c of panels equipped with a color filter, a method of constructing the illumination light sources 71a, 71b, 71c, e.g., of light sources of red, green, and blue and the display elements 81a, 81b, 81c of monochromatic display panels, and so on.

In FIG. 32, it is also possible to increase the number of parallax images presented to the observing eye, by constructing each of the illumination light sources 71a, 71b, 71c of a plurality of unit light sources as illustrated in FIGS. 25A to 25C, 26A to 26C and 27A to 27C, driving the display elements 81a, 81b, 81c in time division, and properly controlling the lighting of the unit light sources and the display images of the display elements.

(Embodiment 8)

Embodiment 8 of the image observation apparatus according to the present invention will be described below.

There are known quick display devices of the self-emission type like EL panels. There are also known display devices of the light source integrated type in which a back light, polarizers, a transmissive liquid crystal panel, etc. are integrated. In the present embodiment the image observation apparatus is constructed as illustrated in FIG. 33, using such a self-emission type or light-source-integrated display device.

Figure 33:
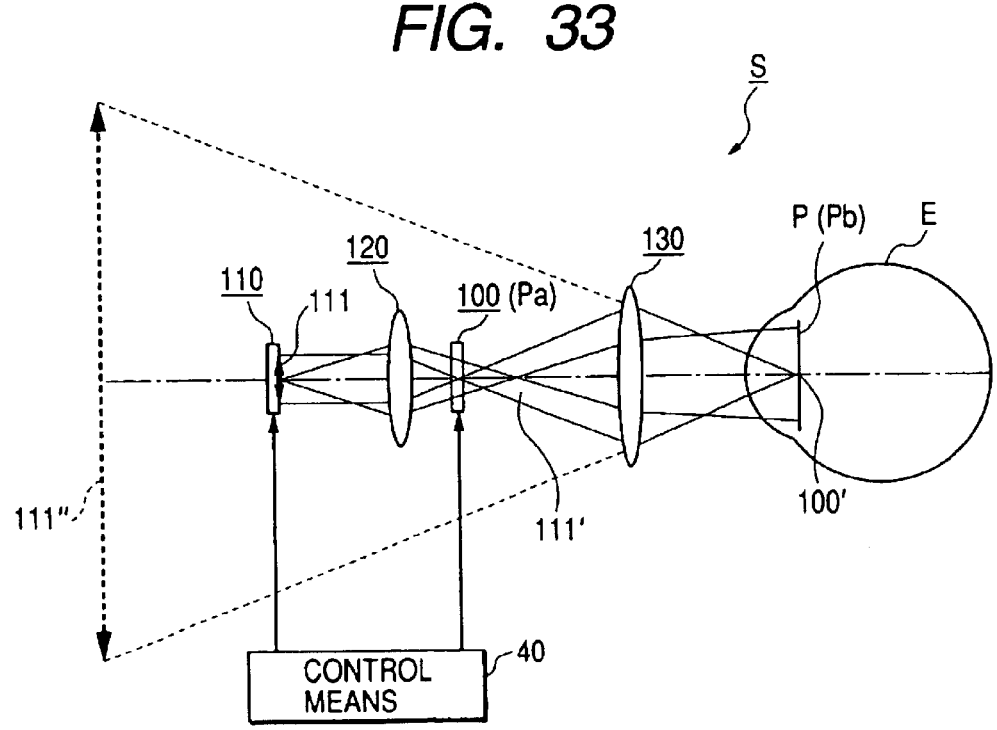
FIG. 33 is a schematic diagram to show the main part of Embodiment 8 of the image observation apparatus according to the present invention.

FIG. 33 is a schematic diagram to show the main part of Embodiment 8 of the image observation apparatus according to the present invention.

The image observation apparatus S according to the present invention has the self-emission type image display means 110 such as an EL panel for displaying the image information 111, a relay optical system 120, the display optical system (eyepiece optical system) 130, a spatial modulation element 100, and the control means 40.

In FIG. 33, the image information 111 displayed on the image display means 110 is focused as an aerial image 111' by the relay optical system 120 and is further focused as an enlarged virtual image 111" by the display optical system 130. The observer substantially aligns the entrance pupil P of the eye with the exit pupil of the display optical system 130 to observe the image 111". The positions, the focal lengths, and so on of the relay optical system 120 and the display optical system 130 are determined so that they form the enlarged virtual image 111" of the image information 111, for example, 2 m ahead of the entrance pupil P.

The spatial modulation element 100 is located at or near the position Pa of the entrance pupil of the display optical system 130, and the display optical system 130 forms an image 100' of the spatial modulation element 100 at or near the position Pb of the exit pupil of the display optical system 130 being in the conjugate relation with the entrance pupil. This permits the state of the incident beam at the position of the entrance pupil of the observer to be changed by controlling positions and areas of the transmitting and intercepting portions of the spatial modulation element 100.

The control means 40 performs the control to properly switch the spatial modulation element 100 and the image display means 110 in time division, so as to inject a plurality of parallax images into the single eye of the observer, based on the principle illustrated in FIGS. 21 to 24, 25A to 25C, 26A to 26C and 27A to 27C, thereby enabling the stereoscopic display of the "super-multiview regions" in the wide angle of view.

(Embodiment 9)

Figure 34:
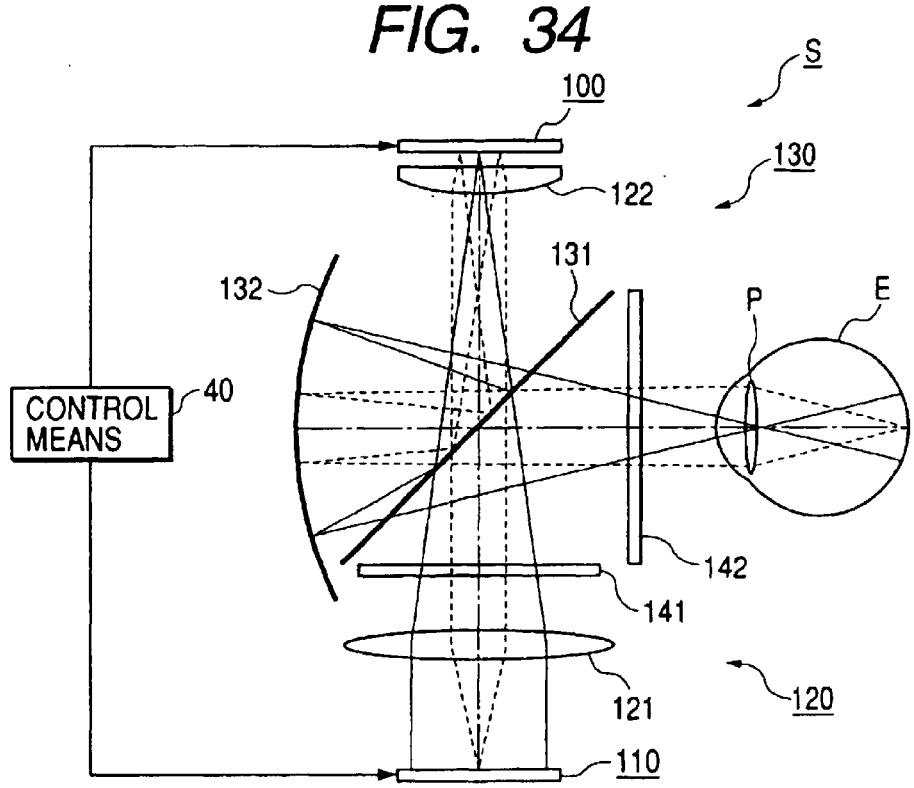
FIG. 34 is a schematic diagram to show the main part of Embodiment 9 of the image observation apparatus according to the present invention.

FIG. 34 is a schematic diagram to show the main part of Embodiment 9 of the image observation apparatus according to the present invention. This apparatus has the self-emission type image display means 110 for displaying the image information, the relay optical system 120, the spatial modulation element 100, the display optical system 130 for guiding the image information to the observing eye E, and the control means 40.

The light emitted from the image display means 110 is converged by a relay lens 121 of the relay optical system 120 and then travels through a polarizer 141 to be converted into linearly polarized light. The linearly polarized light is transmitted in part through a half mirror 131 and the transmitted light is guided through a field lens 122 to the spatial modulation element 100. The spatial modulation element 100 is a reflection type spatial modulation element such as a reflective liquid crystal panel having the pixel structure, which has, for example, the function of reflecting the linearly polarized light incident on the pixels in the "ON" part while rotating the direction of polarization by 90° but reflecting the linearly polarized light incident on the pixels in the "OFF" part while preserving the direction of polarization thereof.

The light reflected by the spatial modulation element 100 forms an aerial image of the image display means 110 and is reflected in part through the half mirror 131. The reflected light is reflected by a concave mirror 132 to be transmitted in part by the half mirror 131 again, and then is guided to a polarizer 142. The polarizer 142 is arranged so that its axis of transmitted polarization is perpendicular to that of the polarizer 141. Since the reflected light from the pixels in the "ON" part of the spatial modulation element 100 has the direction of polarization rotated 90°, it travels through the polarizer 142 to be guided to the observing eye E. However, since the reflected light from the pixels in the "OFF" part of the spatial modulation element 100 has the direction of polarization preserved, it is intercepted by the polarizer 142, so as not to enter the observing eye E. The polarizer 142 also has the function of intercepting the light emitted from the image display means 110, transmitted through the polarizer 141, and partly reflected toward the observing eye E by the half mirror 131, so as to prevent it from entering the observing eye E.

The spatial modulation element 100 is located at the position of the entrance pupil of the display optical system 130, and the display optical system 130 forms an image of the spatial modulation element 100 at the position of the exit pupil of the display optical system 130 being in the conjugate relation with the entrance pupil. The observer substantially aligns the entrance pupil P of the eye with the exit pupil of the display optical system 130 whereby the observer observes the image formed by the relay optical system 120 and the display optical system 130 from the image information displayed on the image display means 110. The positions, the focal lengths, etc. of the relay optical system 120 and the display optical system 130 are determined so that they form an enlarged virtual image of the display element surface of the image display means 110, for example, 2 m ahead of the entrance pupil P.

The control means 40 performs the control to properly switch the spatial modulation element 100 and the image display means 110 in time division, so as to cause a plurality of parallax images to be incident on the single eye of the observer, based on the principle illustrated in FIGS. 21 to 24, 25A to 25C, 26A to 26C and 27A to 27C, thereby enabling the stereoscopic display of the "super-multiview regions" in the wide angle of view.

Since the imaging relation of the pupil can be separated from the imaging relation of the image display means by the use of the field lens 122, it increases degrees of freedom of layout and facilitates decrease of size of apparatus and the like.

Figure 35:
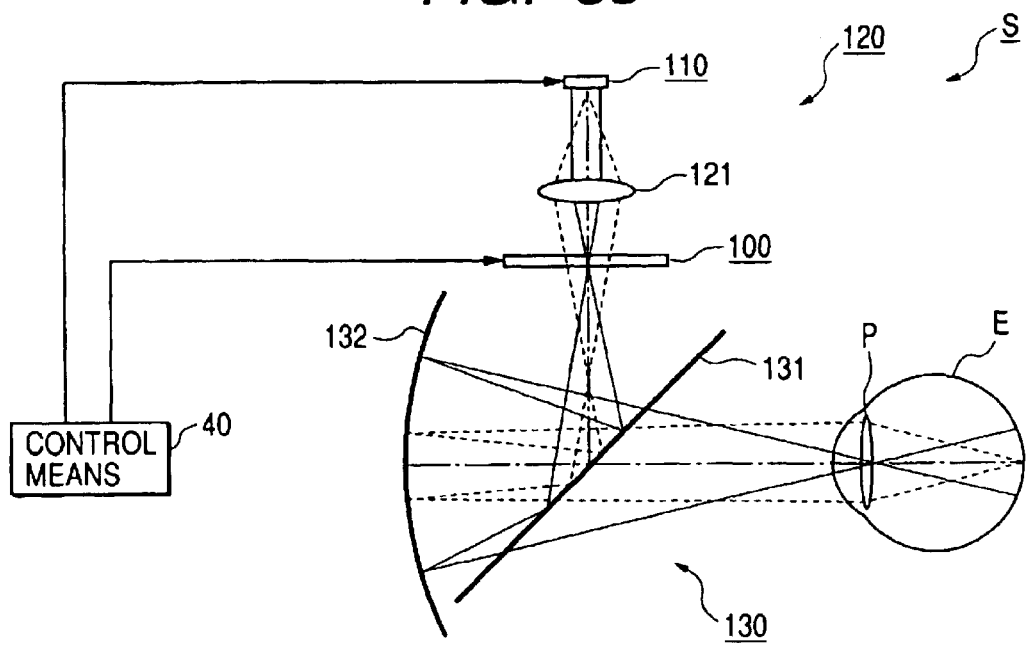
FIG. 35 is a schematic diagram to illustrate the main part of a modification with change in part of Embodiment 9 of the image observation apparatus according to the present invention.

In the embodiment illustrated in FIG. 34, the spatial modulation element 100 was the reflection type element, but a transmission type spatial modulation element 100 may also be used as illustrated in FIG. 35.

In FIG. 35, the elements having the same functions as those in the embodiment illustrated in FIG. 34 are denoted by the same reference symbols and the description thereof is omitted herein. The light emitted from the image display device 110 is guided to the spatial modulation element 100 while being converged by the relay optical system 120. The spatial modulation element 100 is the transmission type spatial modulation element consisting of polarizers, a transmissive liquid crystal panel, and so on. The light transmitted through the spatial modulation element 100 is guided to the observing eye E by the display optical system 130 consisting of the half mirror 131 and the concave mirror 132. The display optical system 130 forms an image of the spatial modulation element 100 at the position of the exit pupil thereof. The observer substantially aligns the entrance pupil P of the eye with the exit pupil of the display optical system 130 whereby the observer observes the image formed by the display optical system 130 from the image information displayed on the image display means 110.

The control means 40 performs the control to properly switch the spatial modulation element 100 and the image display means 110 in time division, so as to cause a plurality of parallax images to be incident on the single eye of the observer, based on the principle illustrated in FIGS. 21 to 24, 25A to 25C, 26A to 26C and 27A to 27C, thereby enabling the stereoscopic display of the "super-multiview regions" in the wide angle of view.

In Embodiments 5 to 9 described above, the position of the pupil of the observer can be detected using the pupil position detecting system (pupil position detecting means) illustrated in FIG. 18.

The pupil position detecting means 150 sends the detected information of pupil position to the control means 40, and the control means 40 controls the illumination means 10 and display means 20, or the spatial modulation element 100 and the display means 110, based on the information.

In another configuration, the control means 40 can be configured to automatically determine the direction of the visual axis of the observer, e.g., from a position of an image including a high-frequency component in the screen, based on the image information from the image input means, calculate an estimated pupil position, and control the illumination means 10 and the display means 20, or the spatial modulation element 100 and the display means 110, based thereon.

Further, when a pair of image observation devices S in each of the above embodiments are provided for the left and right eyes of the observer as illustrated in FIG. 36, it becomes feasible to implement the stereoscopic vision including the binocular parallax and to present a plurality of parallax images to the observing eyes. Therefore, the apparatus can reduce the fatigue due to the contradiction between convergence and accommodation of the observing eyes, which can occur during the observation of the stereoscopic image by use of only the binocular parallax, and permits the observer to observe the stereoscopic image well in the natural state. Particularly, in the construction using the image observation apparatus of the present invention, the beam is incident on the eye without being intercepted even during the gaze at the marginal part of the field, and it thus becomes feasible to implement the display and observation in the wide angle of view and to reproduce the space in the wide range in the depth direction.

In the case wherein a pair of image observation devices according to the present invention are provided for the left and right eyes as illustrated in FIG. 36, when the gazing position is further outside that illustrated in FIG. 27C, the plurality of parallax images fail to enter the observing eyes, but the stereoscopic image can be observed at least by the binocular parallax.

In each of the above embodiments the phrase "spatially divide the exit pupil of the display optical system into a plurality of regions" means as follows; in Embodiments 5 to 7, the illumination light source located at the position of the entrance pupil of the display optical system is comprised of a plurality of unit light sources as illustrated in FIGS. 25A to 25C whereby the images of the unit light sources formed on the exit pupil spatially divide the exit pupil into a plurality of regions; in Embodiments 8 and 9, the spatial modulation element having the two-dimensional pixel structure is located at the position of the entrance pupil of the display optical system whereby the images of the respective pixels of the spatial modulation element formed on the exit pupil spatially divide the exit pupil into a plurality of regions.

The control means to change the position of the beam from the image display means at the position of the entrance pupil of the observing eye is to change the position of the beam from the light source illuminating the image display means in Embodiments 5 to 7. In Embodiments 8, 9, the position of the beam from the image display means is changed by the spatial modulation element provided in the optical path, using the self-emission type image display means.

The present invention is able to achieve the image observation apparatus being capable of implementing the stereoscopic display of the super-multiview regions in the wide angle of view and permitting the observer to well observe the stereoscopic image without fatigue nor dysphoria, and the image observation systems using the apparatus.

In addition, the present invention makes it feasible to implement the stereoscopic display of the "super-multiview regions" in the wide angle of view without need for use of the very quick image display means and image generating means nor many image display means, to simplify and compactify the apparatus, and free the observer from the fatigue and dysphoria during observation.

What is claimed is:

1. An image observation apparatus comprising image display means for displaying a plurality of parallax images, and a display optical system for guiding light from the image display means to an observing eye of an observer, said image observation apparatus having means for spatially dividing an exit pupil of the display optical system into a plurality of regions, and being constructed to substantially align a position of the exit pupil of the display optical system with a position of an entrance pupil of the observing eye, cause parallax images corresponding to the respective regions to be incident on the observing eye, and thereby cause a plurality of parallax images to be incident on the single eye of the observer, wherein an area of a region in the outermost periphery out of the plurality of regions in the divided exit pupil is greater than those of the regions except for that in the outermost periphery.

2. An image observation apparatus comprising image display means for displaying a plurality of parallax images, and a display optical system for guiding light from the image display means to an observing eye of an observer, said image observation apparatus having means for spatially dividing an exit pupil of the display optical system into a plurality of regions, and being constructed to substantially align a position of the exit pupil of the display optical system with a position of an entrance pupil of the observing eye, cause parallax images corresponding to the respective regions to be incident on the observing eye, and thereby cause a plurality of parallax images to be incident on the single eye of the observer, wherein a size of the exit pupil of the display optical system is larger than size of the entrance pupil of the observing eye and a size of a beam from the image display means at the position of the entrance pupil of the observing eye is substantially equal to or smaller than the size of the entrance pupil of the observing eye, said image observation apparatus comprising control means to change a position of the beam from the image display means at the position of the entrance pupil of the observing eye to cause plural parallax images corresponding to respective regions of the exit pupil to be incident on the single eye of the observer.

3. The image observation apparatus according to claim 2, further comprising pupil position detecting means for detecting the position of the pupil of the observer, wherein the position of the beam from the image display means at the position of the entrance pupil of the observing eye is changed by said control means, based on information obtained by the pupil position detecting means.

4. The image observation apparatus according to claim 3, wherein said pupil position detecting means comprises eyeball illuminating means and light receiving means for receiving light reflected by the eyeball from illumination light emitted from the eyeball illuminating means, wherein the eyeball illumination light is infrared light.

5. An image observation apparatus comprising:
image display means for displaying a plurality of parallax images;
a display optical system including an exit pupil;
means for spatially dividing the exit pupil of display optical system into a plurality of regions, said display optical system guiding the parallax images displayed on said image display means to each of the plurality of regions; and
control means for guiding light of the plurality of parallax images into the plurality of regions,
wherein an area of a region in the outermost periphery out of the plurality of regions in the divided exit pupil is greater than an area of regions except for a region in the outermost periphery.

6. The image observation apparatus according to claim 5, wherein the exit pupil of said display optical system and an entrance pupil of the observing eye are positioned to be coplanar.

7. The image observation apparatus according to claim 5, wherein an area of the regions except for regions in the outermost periphery out of the plurality of regions in the divided exit pupil is less than an area of the entrance pupil of the observing eye.

8. An image observation apparatus comprising:
image display means for displaying a plurality of parallax images;
a display optical system including an exit pupil;
means for spatially dividing the exit pupil of the display optical system into a plurality of divided regions having an area less than an area of an entrance pupil of an observing eye, said display optical system guiding the parallax images displayed on said image display means to each of the plurality of regions, and
control means for guiding light of the plurality of parallax images into each corresponding area in the plurality of the divided regions;
wherein a size of the exit pupil of said display optical system is greater than a size of the entrance pupil of the observing eye,
and wherein said control means guides light of the parallax images into the plurality of regions selected from the plurality of the divided regions according to a position of the entrance pupil of the observing eye to cause plural parallax images corresponding to respective regions of the exit pupil to be incident on a single eye of the observer.

9. The image observation apparatus according to claim 8, wherein the exit pupil of said display optical system and the entrance pupil of the observing eye are positioned to be coplanar.

10. The image observation apparatus according to claim 8, further comprising pupil position detecting means for detecting the position of the pupil of the observing eye, wherein said control means selects regions where a light of parallax images is guided based on information obtained by said pupil position detecting means.

11. The image observation apparatus according to claim 10, wherein said pupil position detecting means comprises eyeball illuminating means and light receiving means for receiving light emitted from the eyeball illuminating means and reflected by an eyeball, and wherein an eyeball illumination light is infrared light.

12. The image observation apparatus according to any one of claims 1 to 4, 5 to 9 and 10, comprising illumination means having an illumination light source for illuminating said image display means, wherein said illumination means is located at or near a position optically equivalent to the entrance pupil of said display optical system, the illumination means comprises a plurality of light source elements, images of the plurality of light source elements are formed on a plurality of regions in the exit pupil of the display optical system, the exit pupil of the display optical system is spatially divided into a plurality of irradiation regions, and a display image on said image display means is controlled to switch to one corresponding to each irradiation region.

13. The image observation apparatus according to claim 12, wherein the plurality of light source elements of said illumination light source are comprised of a light-emitting element array.

14. The image observation apparatus according to claim 12, wherein the plurality of light source elements of said illumination light source are comprised of a surface illuminant and a spatial modulation element.

15. The image observation apparatus according to any one of claims 1 to 4, 5 to 9 and 10, wherein said image display means comprises a plurality of display elements, said image observation apparatus comprising at least one illumination means having an illumination light source for illuminating the plurality of display elements, wherein the illumination means is located at or near a position optically equivalent to the entrance pupil of said display optical system, the illumination means comprises a plurality of light source elements, images of the plurality of light source elements are formed on a plurality of regions in the exit pupil of the display optical system, the exit pupil of the display optical system is spatially divided into a plurality of irradiation regions, and parallax images displayed on said plurality of display elements are controlled corresponding to each irradiation region.

16. The image observation apparatus according to claim 15, wherein said illumination means is a plurality of illumination means, incidence of beams into a plurality of regions in the exit pupil of said display optical system is controlled in time division by controlling in time division irradiation of beams from a plurality of light source elements which an illumination light source of each illumination means has, and parallax images displayed on said plurality of display elements are controlled to switch to those corresponding to each region.

17. The image observation apparatus according to claim 15, wherein the plurality of light source elements of said illumination means are comprised of a light-emitting element array.

18. The image observation apparatus according to claim 15, wherein the plurality of light source elements of said illumination means are comprised of a surface illuminant and a spatial modulation element.

19. The image observation apparatus according to any one of claim 1 to 4, 5 to 9 and 10, wherein said image display means comprises a self-emission type image display element or a light-source-integrated type image display element, said display optical system comprises a relay optical system for forming an aerial image of a surface of the image display element and an eyepiece optical system for presenting an enlarged virtual image of the aerial image to the observing eye, a spatial modulation element having a two-dimensional pixel structure is located at or near a position of an entrance pupil of the eyepiece optical system, images of the spatial modulation element divide the exit pupil of said display optical system into a plurality of regions, beams incident to the plurality of regions in the exit pupil of said display optical system are controlled by controlling irradiation of beams from respective pixels of the spatial modulation element, and parallax images displayed on said image display means are controlled to switch to those corresponding to circumstances of incidence of a beam into each region.

20. The image observation apparatus according to claim 19, wherein said spatial modulation element is a transmission type spatial modulation element.

21. The image observation apparatus according to claim 19, wherein said spatial modulation element is a reflection type spatial modulation element.

22. The image observation apparatus according to any one of claims 1 to 4, 5 to 9 and 10, wherein said display optical system comprises a prism body having a decentered, rotationally asymmetric, reflective surface with optical powers differing depending upon azimuth angles.

23. An image observation system comprising a pair of image observation apparatus as set forth in any one of claims 1 to 4, 5 to 9 and 10, for the left and right eyes of the observer.

* * * * *

UNITED STATES PATENT AND TRADEMARK OFFICE
CERTIFICATE OF CORRECTION

PATENT NO. : 7,001,019 B2
APPLICATION NO. : 09/838219
DATED : February 21, 2006
INVENTOR(S) : Akinari Takagi et al.

It is certified that error appears in the above-identified patent and that said Letters Patent is hereby corrected as shown below:

ON THE COVER PAGE
At Item (57) Abstract, line 9, "onto" should read --on--.

COLUMN 15
Line 18, "have" should read --has--.

COLUMN 18
Line 18, "forty nine" should read --forty-nine--.
Line 23, "forty nine" should read --forty-nine--.
Line 32, "forty nine" should read --forty-nine--.

COLUMN 19
Line 2, "forty nine" should read --forty-nine--.
Line 41, "enough" should read --large enough--.

COLUMN 28
Line 53, "size" should read --the size--.

COLUMN 29
Line 14, "display" should read --said display--.

COLUMN 30
Line 8, "claims 1 to 4, 5 to 9 and 10," should read --claims 1 to 10,--.
Line 28, "claims 1 to 4, 5 to 9 and 10," should read --claims 1 to 10,--.
Line 61, "claims 1 to 4, 5 to 9 and 10," should read --claims 1 to 10,--.

UNITED STATES PATENT AND TRADEMARK OFFICE
CERTIFICATE OF CORRECTION

PATENT NO. : 7,001,019 B2
APPLICATION NO. : 09/838219
DATED : February 21, 2006
INVENTOR(S) : Akinari Takagi et al.

It is certified that error appears in the above-identified patent and that said Letters Patent is hereby corrected as shown below:

COLUMN 32
Line 5, "claims 1 to 4, 5 to 9 and 10," should read --claims 1 to 10,--.
Line 11, "1 to 4, 5 to 9 and 10," should read --1 to 10,--.

Signed and Sealed this

Eighteenth Day of September, 2007

JON W. DUDAS
*Director of the United States Patent and Trademark Office*